United States Patent
Georgiou et al.

(10) Patent No.: US 12,144,828 B2
(45) Date of Patent: Nov. 19, 2024

(54) HUMAN KYNURENINASE ENZYMES AND USES THEREOF

(71) Applicant: BOARD OF REGENTS, THE UNIVERSITY OF TEXAS SYSTEM, Austin, TX (US)

(72) Inventors: George Georgiou, Austin, TX (US); Everett Stone, Austin, TX (US); John Blazeck, Austin, TX (US); Christos Karamitros, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 18/296,687

(22) Filed: Apr. 6, 2023

(65) Prior Publication Data
US 2023/0405049 A1 Dec. 21, 2023

Related U.S. Application Data

(62) Division of application No. 16/385,562, filed on Apr. 16, 2019, now Pat. No. 11,648,272.

(60) Provisional application No. 62/658,261, filed on Apr. 16, 2018.

(51) Int. Cl.
| | |
|---|---|
| A61K 35/17 | (2015.01) |
| A61K 38/46 | (2006.01) |
| A61K 47/60 | (2017.01) |
| A61P 35/00 | (2006.01) |
| C07K 14/725 | (2006.01) |
| C07K 16/28 | (2006.01) |

(52) U.S. Cl.
CPC .............. *A61K 35/17* (2013.01); *A61K 38/46* (2013.01); *A61K 47/60* (2017.08); *A61P 35/00* (2018.01); *C07K 14/7051* (2013.01); *C07K 16/2818* (2013.01); *C07K 16/2827* (2013.01); *C12Y 307/01003* (2013.01)

(58) Field of Classification Search
CPC ........ A61K 35/17; A61K 38/46; A61K 47/60; A61P 35/00; C07K 16/2818; C07K 16/2827; C12Y 307/01003
See application file for complete search history.

(56) References Cited

U.S. PATENT DOCUMENTS

| | | |
|---|---|---|
| 7,109,304 B2 | 9/2006 | Hansen et al. |
| 7,714,139 B2 | 5/2010 | Prendergast et al. |
| 8,377,976 B2 | 2/2013 | Combs et al. |
| 8,465,743 B2 | 6/2013 | Rosenberg et al. |
| 9,808,486 B2 | 11/2017 | Georgiou et al. |
| 9,975,959 B2 | 5/2018 | Georgiou et al. |
| 10,772,913 B2 | 9/2020 | Georgiou et al. |
| 11,168,142 B2 | 11/2021 | Georgiou et al. |
| 2003/0194721 A1 | 10/2003 | Mikita et al. |
| 2009/0304666 A1 | 12/2009 | Harrison |
| 2015/0064154 A1 | 3/2015 | Georgiou et al. |
| 2016/0058845 A1 | 3/2016 | Georgiou et al. |
| 2017/0056449 A1 | 3/2017 | Georgiou et al. |
| 2019/0002579 A1 | 1/2019 | Georgiou et al. |
| 2020/0054674 A1 | 2/2020 | Georgiou et al. |
| 2021/0207110 A1 | 7/2021 | Georgiou et al. |
| 2021/0213059 A1 | 7/2021 | Georgiou et al. |

FOREIGN PATENT DOCUMENTS

| | | |
|---|---|---|
| CN | 1442487 | 9/2003 |
| JP | 2006-521378 | 9/2006 |
| JP | 2008-237022 | 10/2008 |
| JP | 2010-504346 | 2/2010 |
| JP | 2016-533753 | 11/2016 |
| WO | WO 2007/004692 | 1/2007 |
| WO | WO 2012/031744 | 3/2012 |
| WO | WO 2012/079000 | 6/2012 |
| WO | WO 2012/099441 | 7/2012 |
| WO | WO 2013/034685 | 3/2013 |
| WO | WO 2013/059593 | 4/2013 |
| WO | WO 2015/031771 | 3/2015 |
| WO | WO 2016/033488 | 3/2016 |
| WO | WO 2017/151860 | 9/2017 |

OTHER PUBLICATIONS

"KYNU_Human," UniProt Submission Q16719, dated Jul. 24, 2013.
"KYNU_Human," UniProt Submission Q16719.1, dated Nov. 30, 2016.
"kynureninase (EC 3.7.1.3)—human", GenBank accession No. G02652, 1999.
"SIDS2vsH1YAV1," UniProt 201609, dated Mar. 21, 2012.
Adams et al. "The kynurenine pathway in brain tumor pathogenesis." *Cancer Research* 72.22 (2012): 5649-5657.
Alberati-Giani et al., "Isolation and expression of a cDNA clone encoding human kynureninase," *Eur J Biochem.*, 239:460-468, 1996.
Chen and Guillemin, "Kynurenine pathway metabolites in humans: disease and healthy states," *Int. J. Tryptophan Res.*, 2:1-19, 2009.
Curran et al., "PD-1 and CTLA-4 combination blockade expands infiltrating T cells and reduces regulatory T and myeloid cells within B16 melanoma tumors," *Proc. Natl. Acad. Sci. U S A*, 107:4275-4280, 2010.
De Jong et al., "Serum tryptophan and kynurenine concentrations as parameters for indoleamine 2,3-dioxygenase activity in patients with endometrial, ovarian, and vulvar cancer," *Int. J. Gynecol. Cancer*, 21(7):1320-1327, 2011.

(Continued)

*Primary Examiner* — Paul J Holland
(74) *Attorney, Agent, or Firm* — Parker Highlander PLLC

(57) ABSTRACT

Methods and compositions related to the use of a protein with kynureninase activity are described. For example, in certain aspects there may be disclosed a modified kynureninase capable of degrading kynurenine. Furthermore, certain aspects of the invention provide compositions and methods for the treatment of cancer with kynurenine depletion using the disclosed proteins or nucleic acids.

18 Claims, 4 Drawing Sheets

Specification includes a Sequence Listing.

(56) References Cited

OTHER PUBLICATIONS

Della Chiesa et al., "The tryptophan catabolite L-kynurenine inhibits the surface expression of NKp46-and NKG2D-activating receptors and regulates NK-cell function," *Blood*, 108(13):4118-4125, 2006.
Disis et al., "Use of tumor-responsive T cells as cancer treatment," *Lancet*, 373:673-83, 2009.
Duval et al., "Adoptive transfer of allogeneic cytotoxic T lymphocytes equipped with a HLA-A2 restricted MART-1 T-cell receptor: a phase I trial in metastatic melanoma," *Clin. Cancer Res.*, 12:1229-36, 2006.
Extended European Search Report issued in corresponding European Application No. 18204264, mailed on Apr. 25, 2019.
Extended European Search Report issued in European Application No. 17760774.4, mailed on Jul. 22, 2019.
Extended European Search Report issued in European Patent Application No. 14840339.7, dated Mar. 28, 2017.
Gailani et al., "Studies on tryptophan metabolism in patients with bladder cancer," *Cancer Research.*, 33:1071-1077, 1973.
Godin-Ethier et al., "Indoleamine 2, 3-Dioxygenase Expression in Human Cancers: Clinical and Immunologic Perspectives," *Clinical Cancer Research*, 17(22):6985-6991, 2011.
Holmgaard et al., "Indoleamine 2, 3-dioxygenase is a critical resistance mechanism in antitumor T cell immunotherapy targeting CTLA-4," *The Journal of Experimental Medicine*, 210:1389-1402, 2013.
Hoyos et al., "Genetic modification of human T lymphocytes for the treatment of hematologic malignancies," *Haematologica.*, 97(11):1622-31, 2012.
International Preliminary Report on Patentability issued in International Application No. PCT/US2014/053437, mailed Mar. 10, 2016.
International Preliminary Report on Patentability issued in International Application No. PCT/US2015/047475, mailed Mar. 9, 2017.
International Search Report and Written Opinion issued in International Application No. PCT/US2014/053437, mailed Mar. 10, 2015.
International Search Report and Written Opinion issued in International Application No. PCT/US2015/047475, mailed Feb. 2, 2016.
International Search Report and Written Opinion issued in PCT Application No. PCT/US2019/027623, mailed on Aug. 22, 2019.
Kaper et al., "Nanosensor detection of an immunoregulatory tryptophan influx/kynurenine efflux cycle," *PLoS Biology*, 5(10):e257, 2007.
Lima et al., "Crystal Structure of *Homo Sapiens* Kynureninase," *Biochemistry*, 46(10):2735-2744, 2007.
Lima et al., "Crystal structure of the *Homo sapiens* kynureninase-3-hydroxyhippuric acid inhibitor complex: insights into the molecular basis of kynureninase substrate specificity," *J. Med. Chem.*, 52(2):389-396, 2009.
Lipowska-Bhalla et al., "Targeted immunotherapy of cancer with CAR T cells: achievements and challenges," *Cancer Immunology Immunotherapy*, 61(7):953-962, 2012.
Lob et al., "Inhibitors of indoleamine-2,3-dioxygenase for cancer therapy: can we see the wood for the trees?" *Nat. Rev. Cancer*, 9(6):445-452, 2009.
Mandi and Vecsei, "The kynurenine system and immunoregulation," *J. Neural Transm.*, 119(2):197-209, 2012.
Mezrich et al., "An interaction between kynurenine and the aryl hydrocarbon receptor can generate regulatory T cells," *The Journal of Immunology*, 185(6):3190-3198, 2010.
Office Communication issued in Chinese Application No. 201480053899.1, mailed Feb. 15, 2019. (English Translation).
Office Communication issued in Japanese Application No. 2016-537898, mailed Sep. 20, 2017. (English Translation).
Office Communication issued in Japanese Application No. 2017-511675, mailed Jun. 27, 2019. (English Translation).
Office Communication issued in Japanese Application No. 2018-042760, mailed Jan. 16, 2019. (English Translation).
Office Communication Issued in U.S. Appl. No. 14/473,040, mailed Nov. 23, 2016.
Office Communication issued in U.S. Appl. No. 15/351,060, dated Dec. 12, 2016.
Office Communication issued in U.S. Appl. No. 14/839,293, dated Oct. 19, 2017.
Office Communication issued in U.S. Appl. No. 14/839,293, dated Apr. 14, 2017.
Office Communication issued in U.S. Appl. No. 14/839,293, dated Jan. 6, 2017.
Office Communication issued in U.S. Appl. No. 14/473,040, dated Jul. 3, 2017.
Office Communication issued in U.S. Appl. No. 14/473,040, dated Jul. 6, 2016.
Office Communication issued in U.S. Appl. No. 15/351,060, dated Mar. 9, 2018.
Office Communication issued in U.S. Appl. No. 15/351,060, dated Jun. 26, 2017.
Opitz et al., "An endogenous tumour-promoting ligand of the human aryl hydrocarbon receptor," *Nature*, 478(7368):197-203, 2011.
Opitz et al., "The Indoleamine-2, 3-Dioxygenase (IDO) Inhibitor 1-Methyl-D-tryptophan Upregulates IDO1 in Human Cancer Cells," *PLoS One*, 6(5):e19823, 2011.
Phillips, "Structure and mechanism of kynureninase," *Archives of Biochemistry and Biophysics*, 544:69-74, 2014.
Phillips, "Structure, mechanism, and substrate specificity of kynureninase", *Biochimica et Biophysica Acta*, 1814:1481-1488, 2011.
Pilotte et al., "Reversal of tumoral immune resistance by inhibition of tryptophan 2,3-dioxygenase," *Proc. Natl. Acad. Sci. U S A*, 109(7):2497-2502, 2012.
Platten et al., "Cancer immunotherapy by targeting IDO1/TDO and their downstream effectors," *Front. Immunol.*, 5:673, 2015.
Prendergast, "Cancer: Why tumours eat tryptophan," *Nature*, 478(7368):192-194, 2011.
Rabinkov et al., "Alliinase: structural peculiarities and applying for targeted therapy: SW02. W10-4." *The Febs Journal* 280.1 (2013).
Response filed in U.S. Appl. No. 14/839,293, dated Mar. 6, 2017.
Rutella et al., "Targeting indoleamine 2,3-dioxygenase (IDO) to counteract tumour-induced immune dysfunction: from biochemistry to clinical development," *Endocr. Metab. Immune Disord. Drug Targets*, 9(2):151-177, 2009.
Schottler et al., "Protein engineering of the restriction endonuclease EcoRV—structure-guided design of enzyme variants that recognize the base pairs flanking the recognition site," *Eur. J. Biochem.*, 258(1):184-91, 1998.
Shin et al., "Modulation of natural killer cell antitumor activity by the aryl hydrocarbon receptor," *Proc. Natl. Acad. Sci. U S A*, 110(30):12391-12396, 2013.
Simpson et al., "Fc-dependent depletion of tumor-infiltrating regulatory T cells co-defines the efficacy of anti-CTLA-4 therapy against melanoma," *J. Exp. Med.*, 210(9):1695-1710, 2013.
Singh et al., "Protein Engineering Approaches in the Post-Genomic Era," Current Protein and Peptide Science, 18:1-11, 2017.
Song et al., "L-Kynurenine-induced apoptosis in human NK cells is mediated by reactive oxygen species," *International Immunopharmacology*, 11(8):932-938, 2011.
Stone et al., "Abstract LB-226: Depletion of kynurenine using an engineered therapeutic enzyme potently inhibits cancer immune checkpoints both as a monotherapy and in combination with anti-PD-1," Proceedings of the AACR 106th Annual Meeting, Philadelphia, PA, Apr. 18-22, 2015, Cancer *Research*, 75(15 Supplement):LB-226-LB-226, Aug. 2015.
Supplementary European Search Report issued in European Patent Application No. 15834988.6, dated Jan. 16, 2018.
Toma et al., "Cloning and recombinant expression of rat and human kynureninase," *FEBS Letters.*, 408(1):5-10, 1997.
UniProt_201609 Acc#H1YAV1 Lucas et al., Mar. 21, 2012. Alignment with SEQ ID No. 33.
Veronese et al., "Peptide and protein PEGylation: a review of problems and solutions," *Biomaterials*, 22(5):405-417, 2001.

(56) References Cited

OTHER PUBLICATIONS

Walsh et al., "Purification and biochemical characterization of some of the properties of recombinant human kynurinase", *Eur. J. Biochem.*, 269:2069-2074, 2002.

Yao et al., "Serum metabolic profiling and features of papillary thyroid carcinoma and nodular goiter," *Mol. Biosyst.*, 7(9):2608-2614, 2011.

Yoshikawa et al., "Serum concentration of L-kynurenine predicts the clinical outcome of patients with diffuse large B-cell lymphoma treated with R-CHOP," *Eur. J. Haematol.*, 84(4):304-309, 2010.

Zhang et al., "Propagated Perturbations from a Peripheral Mutation Show Interactions Supporting WW Domain Thermostability," *Structure*, 26:1474-1485, 2018.

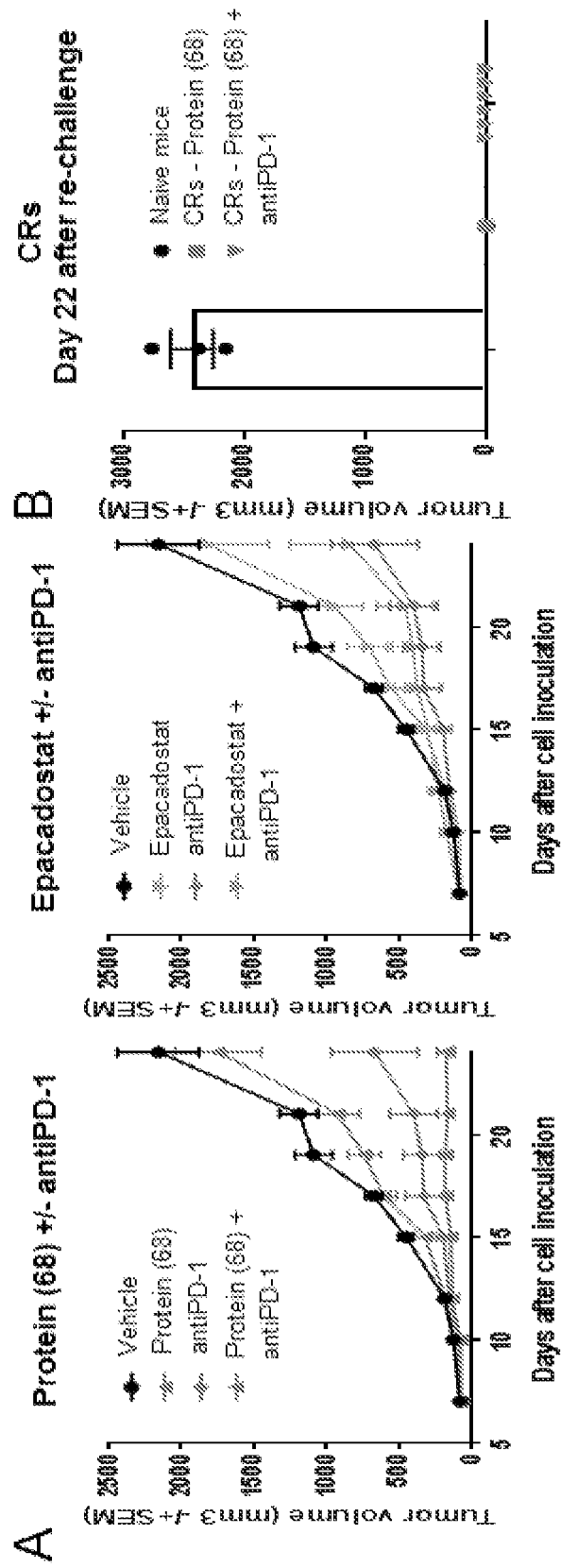
FIGS. 2A-B

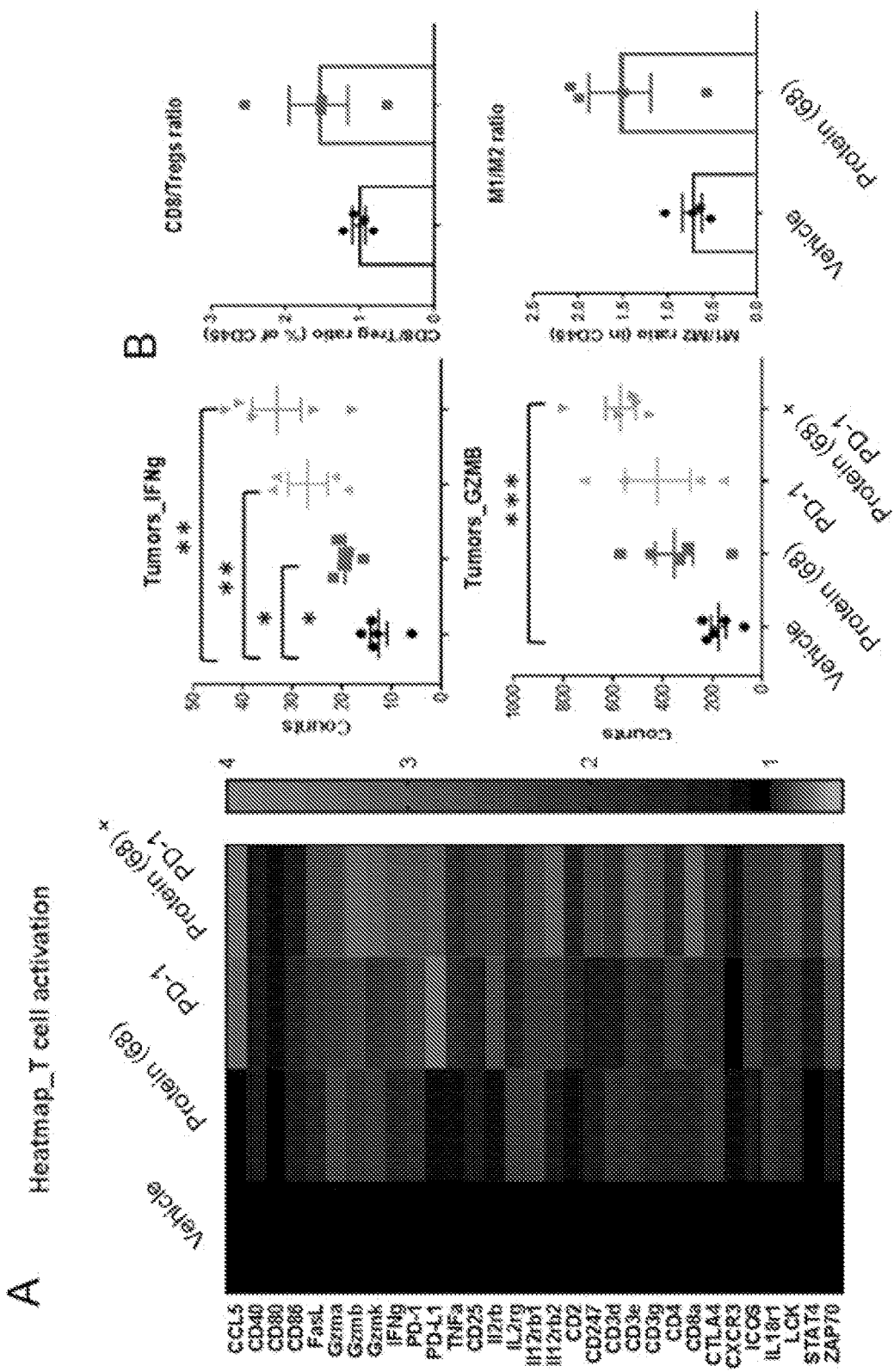
FIGS. 3A-B

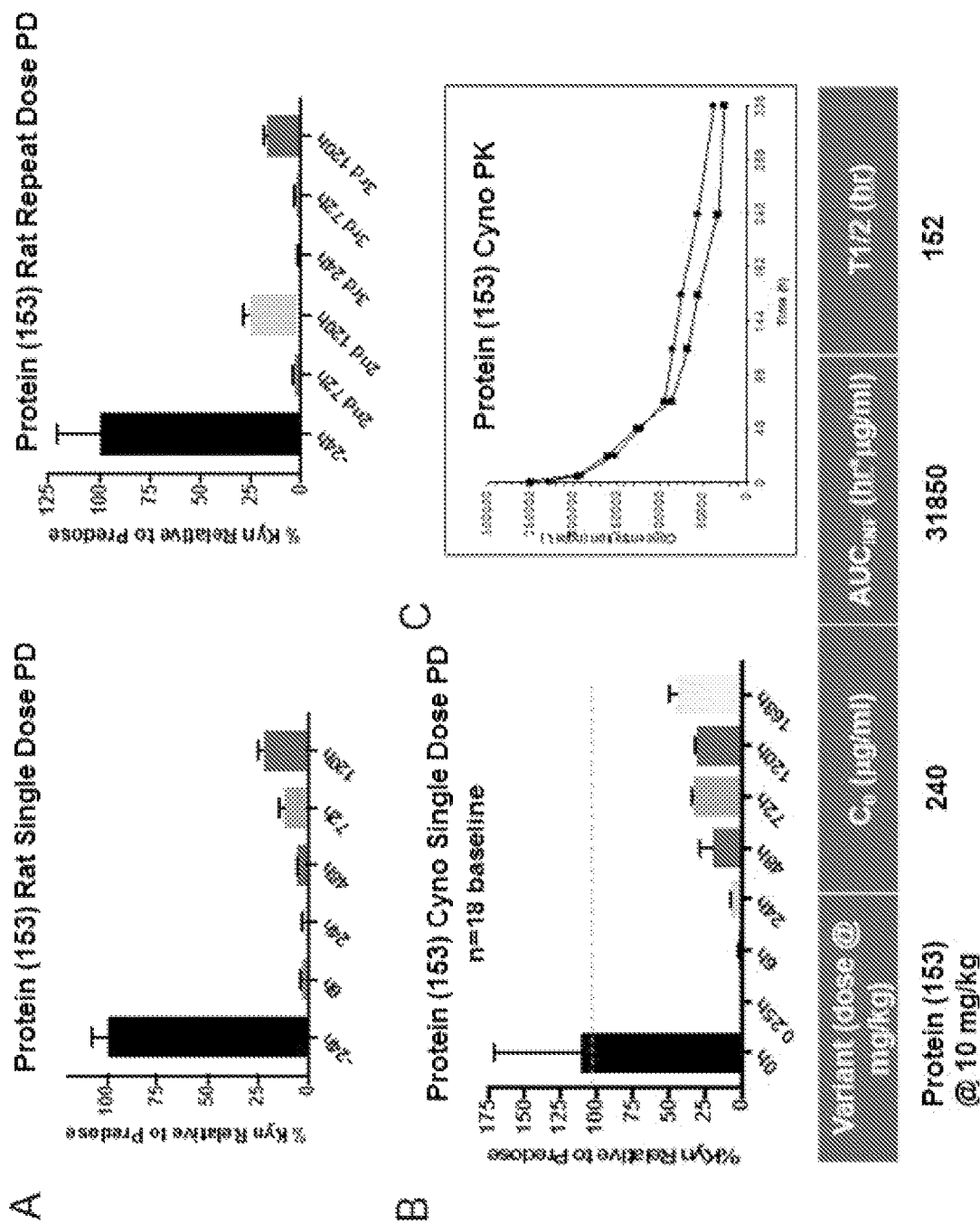
FIGS. 4A-C

```
                                       SEQUENCE LISTING

Sequence total quantity: 3
SEQ ID NO: 1              moltype = AA  length = 465
FEATURE                   Location/Qualifiers
source                    1..465
                          mol_type = protein
                          organism = Homo sapiens
SEQUENCE: 1
MEPSSLELPA DTVQRIAAEL KCHPTDERVA LHLDEEDKLR HFRECFYIPK IQDLPPVDLS   60
LVNKDENAIY FLGNSLGLQP KMVKTYLEEE LDKWAKIAAY GHEVGKRPWI TGDESIVGLM  120
KDIVGANEKE IALMNALTVN LHLLMLSFFK PTPKRYKILL EAKAFPSDHY AIESQLQLHG  180
LNIEESMRMI KPREGEETLR IEDILEVIEK EGDSIAVILF SGVHFYTGQH FNIPAITKAG  240
QAKGCYVGFD LAHAVGNVEL YLHDWGVDFA CWCSYKYLNA GAGGIAGAFI HEKHAHTIKP  300
ALVGWFGHEL STRFKMDNKL QLIPGVCGFR ISNPPILLVC SLHASLEIFK QATMKALRKK  360
SVLLTGYLEY LIKHNYGKDK AATKKPVVNI ITPSHVEERG CQLTITFSVP NKDVFQELEK  420
RGVVCDKRNP NGIRVAPVPL YNSFHDVYKF TNLLTSILDS AETKN                 465

SEQ ID NO: 2              moltype = AA  length = 465
FEATURE                   Location/Qualifiers
```

```
source                  1..465
                        mol_type = protein
                        organism = synthetic construct
SEQUENCE: 2
MEPSSLELPA DTVQRIAAEL KCHPTDERVA LHLDEEDKLR HFRECFYIPK IQDLPPVDLS    60
LVNKDENAIY FNGNSLGLQP KMVKTYLEEE LDKWAKIARY GWRHGKPPWI TYDESIVGLM   120
KDIVGANEKE IALMNALTVN LHLLMLSFFK PTPKRYKILL EAKAFPSDHY AIESQLQLHG   180
LNPEESMRMI KPREGEETLR IEDILEVIEK EGDSIAVILF SGVHFYTGQH FNIPAITKAG   240
QAKGCYVGWD LAHAVGNVEL YLHDWGVDFA CWCSYKYLNA GPGGIAGAFI HEKHAHTIKP   300
ALVGWWGHEL STRFKMDNKL QLIPGVCGFR SSTPPILLVC SLHASLEIFK QATMKALRKK   360
SVLLTGYLEY LIKHNYGKDK AATKKPVVNI ITPSHVEERG CQLTITFNVP NKDVFQELEK   420
RGVVCDKRNP NGIRVTPVPL YNSFHDVYKF TNLLTSILDS AETKN                  465

SEQ ID NO: 3            moltype = AA  length = 465
FEATURE                 Location/Qualifiers
source                  1..465
                        mol_type = protein
                        organism = synthetic construct
SEQUENCE: 3
MEPSSLELPA DTVQRIAAEL KCHPTDERVA LHLDEEDKLR HFRECFYIPK IQDLPPVDLS    60
LVNKDENAIY FNGNSLGLQP KMVKTYLEEE LDKWAKIARY GWRHGKPPWI TYDESIVGLM   120
KDIVGANEKE IALMNALTVN LHLLMLSFFK PTPKRYKILL EAKAFPSDHY AIESQLQLHG   180
LNPEESMRMI KPREGEETLR IEDILEVIEK EGDSIAVILF SGVHFYTGQH FNIPAITKAG   240
QAKGCYVGFD LAHAVGNVEL YLHDWGVDFA CWCSYKYLNA GPGGIAGAFI HEKHAHTIKP   300
ALVGWWGHEL STRFKMDNKL QLIPGVCGFR SSTPPILLVC SLHASLEIFK QATMKALRKK   360
SVLLTGYLEY LIKHNYGKDK AATKKPVVNI ITPSHVEERG CQLTITFNVP NKDVFQELEK   420
RGVVCDKRNP NGIRVTPVPL YNSFHDVYKF TNLLTSILDS AETKN                  465
```

HUMAN KYNURENINASE ENZYMES AND USES THEREOF

This application is a divisional of U.S. patent application Ser. No. 16/385,562, filed Apr. 16, 2019, which claims the benefit of U.S. Provisional Patent Application No. 62/658,261, filed Apr. 16, 2018, the entirety of each of which is incorporated herein by reference.

This invention was made with government support under Grant No. R01 CA154754 awarded by the National Institutes of Health. The U.S. government has certain rights in the invention.

This application contains a Sequence Listing XML, which has been submitted electronically and is hereby incorporated by reference in its entirety. Said Sequence Listing XML, created on Apr. 5, 2023, is named UTSBP1194USD1.xml and is 5,004 bytes in size.

BACKGROUND OF THE INVENTION

1. Field of the Invention

The present invention relates generally to the field of molecular biology and oncology. More particularly, it concerns engineered kynureninase enzymes and methods for using the same.

2. Description of Related Art

Kynurenine is a metabolite of the amino acid Tryptophan generated via the action of either indolamine 2,3 dioxygenase (IDO) or tryptophan 2,3 dioxygenase (TDO). Kynurenine exerts multiple effects on cell physiology; one of the most important of which is as a modulator of T cell responses. Many tumor cells regulate the synthesis of IDO and/or TDO enzymes to elevate the local concentration of Kynurenine which is accompanied with depletion of Tryptophan. High levels of Kynurenine, in turn serve as a powerful way to inhibit the function of tumor infiltrating T cells that would otherwise attack the tumor.

The significance of Kynurenine production in cancer is well recognized and has led to the development of inhibitors of the Kynurenine-generating enzymes IDO and TDO; at least one of these compounds are currently undergoing Phase II clinical evaluation. However, IDO or TDO inhibition is problematic for cancer therapy because: (1) there are two isoforms of IDO and together with TDO, the inhibition of all possible pathways for Kynurenine generation at present requires the generation of multiple small molecule inhibitors; (2) resistance to inhibition can arise.

The human Kynureninase has a strong preference for the degradation of 3'OH Kynurenine which is degraded with a catalytic efficiency (Kcat/Km) about a 1,000 higher than that displayed for Kynurenine degradation. In contrast some bacterial enzymes such as the enzyme from *P. fluorescens* have strong preference for Kynurenine over 3'OH Kynurenine. For therapeutic purposes it is essential to have an agent (i.e. a therapeutic enzyme) that has the requisite pharmacological properties for in vivo applications in humans. These include: (i) high catalytic activity for Kynurenine, (ii) enhanced stability to deactivation in serum in order to achieve prolonged depletion of Kynurenine in serum and tissues upon single dose injection

SUMMARY OF THE INVENTION

Aspects of the present invention overcome a major deficiency in the art by providing enzymes that comprise engineered polypeptide sequences capable of degrading L-kynurenine, having a high degree of sequence identity with the human enzyme to avoid the elicitation of adverse immune responses and displaying favorable pharmacokinetics in serum as desired for cancer therapy. In PCT/US2014/053437, the inventors disclosed mutant human kynureninase (also referred to herein as h-KYNase or HsKYN) enzymes having up to 24-fold higher catalytic efficiency for the degradation of KYN relative to the wild-type human enzyme. There is a need for the discovery of mutant h-KYNase enzymes having higher catalytic activity and stability in human serum relative to those disclosed in PCT/US2014/053437. Aspects of the present application addresses this need and discloses mutant enzymes having higher catalytic efficiencies and also mutant enzymes having higher catalytic activity than the wild type h-KYNase as well as enzymes with enhanced serum stability.

In a first embodiment, the invention provides an isolated, modified human kynureninase enzyme, said modified enzyme having an amino acid sequence least 80%, 81%, 82%, 83%, 84%, 85%, 86%, 87%, 88%, 89%, 90%, 91%, 92%, 93%, 94%, 95%, 96%, 97%, 98%, or 99% identity to a human kynureninase enzyme of SEQ ID NO: 1, 2, 3 or one of the polypeptides provided in Table 1 and comprising at least one substitution (relative to sequence of SEQ ID NO: 1) selected from the group consisting of L8P, K38E, Y47L, I48F, K50Q, I51M, S60N, K64N, D65G, E66K, N67D, N67P, D67S, A68F, A68T, A68V, F71L, F71M, L72N, K84E, E88N, E89K, E89S, E90Q, D92E, K93N, K93T, A95H, A95Q, K96N, I97H, I97L, I97V, A98G, A99G, A99I, A99R, A99S, A99T, A99V, Y100N, Y100S, Y100T, G101A, H102W, E103F, E103H, E103N, E103Q, E103R, E103V, E103W, V104D, V104E, V104F, V104H, V104K, V104L, V104R, G105A, G105H, G105S, G105T, E106D, K106D, K106E, K106H, K106N, R107P, R107S, P108R, I110A, I110F, I110L, I110M, I110T, T111D, T111H, T111N, T111R, G112A, G112C, G112D, G112K, G112L, G112M, G112Q, G112R, G112S, G112T, G112Y, N127K, I131V, A132V, L133V, A136T, L137T, T138S, N140D, H142Q, Q14R, Y156H, K163T, D168E, H169R, Q175L, I183F, I183L, I183P, I183S, E184A, E184D, E184R, E184T, E184V, E185T, M187L, M189I, K191A, K191G, K191H, K191M, K191N, K191R, K191S, K191T, K191W, E197A, E197D, E197F, E197K, E197M, E197Q, E197S, E197T, E197V, I201C, I201E, I201F, I201H, I201L, I201S, I201T, I201V, H203K, L219M, L219W, F220L, V223I, F225Y, H230F, H230L, H230Y, N232S, Y246F, F249W, D250E, S274A, S274C, S274G, S274N, S274T, L278M, A280G, A280S, A280T, G281S, A282M, A282P, G284N, 1285L, V303L, V303S, F306W, F306Y, S311N, K315E, D317E, D317K, I331C, I331L, I331N, I331S, I331T, I331V, N333T, P334N, P335T, L337T, L338A, L338Q, S341I, K373E, K373N, N375A, N375H, Y376C, Y376F, Y376L, K378G, K378P, K378Q, K378R, K380G, K380S, A382G, A382R, A382T, T383S, K384G, K384N, P386K, P386S, V387L, N389E, 1405L, F407Y, S408D, S408N, N411R, D413S, D413V, Q416T, E419A, E419L, K420E, R421N, V424L, K427M, N429E, G432A and A436T. In some aspects, the amino acid sequence is at least 90%, 91%, 92%, 93%, 94%, 95%, 96%, 97%, 98%, or 99% identical to the amino acid sequence of SEQ ID NO: 1, 2 or 3; or at least 90%, 91%, 92%, 93%, 94%, 95%, 96%, 97%, 98%, or 99% identical to one enzyme of Table 1. In certain aspects, the enzyme may comprise a substitution at A282 (e.g., A282M or A282P), F306 (e.g., F306W or F306Y) or F249, such as F249W. In further aspects, the enzyme may comprise the L72N substitution. In still further aspects, the enzyme may comprise the F306W substitution. In specific aspects, the enzyme may comprise the H102W and N333T substitutions. In another aspect, the enzyme may comprise a substitution at A99. In some aspects, the enzyme may comprise a substitution at G112. In certain specific aspects, the enzyme comprises a substitution at E103. In other aspects, the enzyme comprises a substitution at V104. In further aspects, the enzyme may comprise a substitution at S408. In several aspects, the enzyme may comprise the I183P substitution. In some particular aspects, the enzyme may comprise the R107P substitution. In another specific aspect, the enzyme may comprise the A436T substitution.

In still further aspects, the enzyme may comprise at least one substitution selected from L72N, H102W, A282P, F306W, I331S and N333T. In certain aspects, the enzyme comprises at least two, three, four or five substitutions selected from L72N, H102W, A282P, F306W, I331S and N333T. In some aspects, the enzyme may comprise the substitutions L72N, H102W, A282P, F306W, I331S and N333T. In an additional aspect, the enzyme has a catalytic activity relative the KYN (kcat/kM) of at least 8000 $M^{-1}s^{-1}$. In other aspects, the enzyme has a catalytic activity relative the KYN (kcat/kM) of between about 8000 $M^{-1}s^{-1}$ and 40000 $M^{-1}s^{-1}$; 10000 $M^{-1}s^{-1}$ and 40000 $M^{-1}s^{-1}$; 20000 $M^{-1}s^{-1}$ and 40000 $M^{-1}s^{-1}$; or 25000 $M^{-1}s^{-1}$ and 35000 $M^{-1}s^{-1}$.

In still further aspects, the polypeptide comprises an amino acid sequence is at least 90%, 91%, 92%, 93%, 94%, 95%, 96%, 97%, 98%, or 99% identical to the amino acid sequence of one of the polypeptides of Table 1. In specific aspects, the polypeptide comprises an amino acid sequence 100/6 identical to one of the polypeptides of Table 1. In yet still further aspects, the polypeptide comprises an amino acid sequence is at least 90%, 91%, 92%, 93%, 94%, 95%, 96%, 97%, 98%, or 99% identical to the amino acid sequence of SEQ ID NO: 2. In specific aspects the polypeptide comprises an amino acid sequence 100% identical to SEQ ID NO: 2. In certain aspects, the amino acid sequence is at least 90%, 91%, 92%, 93%, 94%, 95%, 96%, 97%, 98%, or 99% identical to the amino acid sequence of SEQ ID NO: 3. In specific aspects the polypeptide comprises an amino acid sequence 100% identical to SEQ ID NO. 3.

In a further aspect a kynureninase enzymes of the embodiments further comprises one of the amino acid substitutions disclosed in WO/2015/031771, WO/2016/033488 or WO/2017/151860, each of which is incorporated herein by reference in its entirety.

In further aspects, there are provided polypeptides comprising either a native or modified human or primate kynureninase capable of degrading KYN. In some embodiments, the polypeptides are capable of degrading KYN under physiological conditions. For example, the polypeptides have a catalytic efficiency for KYN ($k_{cat}/K_M$) of at least or about 100, 200, 300, 400, 500, 600, 700, 800, 900, 1000, 2000, 3000, 4000, 5000, 6000, 7000, 8000, 9000, $10^4$, $10^5$, $10^6$ $M^{-1}s^{-1}$ or any range derivable therein.

A modified polypeptide as discussed above may be characterized as having a certain percentage of identity as compared to an unmodified polypeptide (e.g., a native polypeptide, such as human kynureninase of SEQ ID NO: 1) or to any polypeptide sequence disclosed herein. For example, the unmodified polypeptide may comprise at least, or up to, about 150, 200, 250, 300, 350, 400, 450 or 465 residues (or any range derivable therein) of a native kynureninase. The percentage identity may be about, at most or at least 65%, 70%, 75%, 80%, 85%, 90%, 95%, 96%, 97%, 98%, or 99% (or any range derivable therein) between the modified and unmodified polypeptides, or between any two sequences in comparison. It is also contemplated that percentage of identity discussed above may relate to a particular modified region of a polypeptide as compared to an unmodified region of a polypeptide. For instance, a polypeptide may contain a modified or mutant substrate recognition site of a kynureninase that can be characterized based on the identity of the amino acid sequence of the modified or mutant substrate recognition site of the kynureninase to that of an unmodified or mutant kynureninase from the same species or across the species. A modified or mutant human polypeptide characterized, for example, as having at least 90% identity to an unmodified kynureninase means that at least 90% of the amino acids in that modified or mutant human polypeptide are identical to the amino acids in the unmodified polypeptide.

Such an unmodified polypeptide may be a native kynureninase, particularly a human isoform or other primate isoforms. For example, the native human kynureninase may have the sequence of SEQ ID NO: 1. Non-limiting examples of other native primate kynureninase include *Pongo abelii* kynureninase (Genbank ID: XP_009235962.1, GI: 686708656), *Macaca fascicularis* kynureninase (Genbank ID: EHH54849.1, GI: 355750522), and *Pan troglodytes* kynureninase (Genbank ID: XP_003309314.1, GI: 332814521). Exemplary native polypeptides include a sequence having about, at most or at least 65%, 70%, 75%, 80%, 85%, 90%, 95%, 96%, 97%, 98%, 99% or 100% identity (or any range derivable therein) of SEQ ID NO:1. For example, the native polypeptide may comprise at least or up to about 10, 20, 30, 40, 50, 60, 70, 80, 90, 100, 150, 200, 250, 300, 350, 400, 450 or 465 residues (or any range derivable therein) of the sequence of SEQ ID NO:1.

In some aspects, polypeptides of the embodiments comprising a kynureninase linked to a heterologous amino acid sequence. For example, the kynureninase may be linked to the heterologous amino acid sequence as a fusion protein. In a particular embodiment, the kynureninase is linked to amino acid sequences, such as an IgG Fc, albumin, an albumin binding protein, or an XTEN polypeptide for increasing the in vivo half-life.

To increase serum persistence, the kynureninase may be linked to one or more polyether molecules. In a particular embodiment, the polyether is polyethylene glycol (PEG). The polypeptide may be linked (e.g., covalently) to PEG via specific amino acid residues, such as lysine or cysteine. For therapeutic administration, such a polypeptide comprising the kynureninase may be dispersed in a pharmaceutically acceptable carrier.

In some aspects, a nucleic acid encoding such a kynureninase is contemplated. In some embodiments, the nucleic acid has been codon optimized for expression in bacteria. In particular embodiments, the bacteria are *E. coli*. In other aspects, the nucleic acid has been codon optimized for expression in fungus (e.g., yeast), insects, or mammals. In further aspects, there are provided vectors, such as expression vectors, containing such nucleic acids. In particular embodiments, the nucleic acid encoding the kynureninase is operably linked to a promoter, including but not limited to heterologous promoters. In one embodiment, a kynureninase is delivered to a target cell by a vector (e.g., a gene therapy vector). Such viruses may have been modified by recombinant DNA technology to enable the expression of the kynureninase-encoding nucleic acid in the target cell. These vectors may be derived from vectors of non-viral (e.g., plasmids) or viral (e.g., adenovirus, adeno-associated virus, retrovirus, lentivirus, herpes virus, or vaccinia virus) origin.

Non-viral vectors are preferably complexed with agents to facilitate the entry of the DNA across the cellular membrane. Examples of such non-viral vector complexes include the formulation with polycationic agents which facilitate the condensation of the DNA and lipid-based delivery systems. An example of a lipid-based delivery system would include liposome based delivery of nucleic acids.

In still further aspects, the present invention further contemplates host cells comprising such vectors. The host cells may be bacteria (e.g., *E. coli*), fungal cells (e.g., yeast), insect cells, or mammalian cells.

In some embodiments, the vectors are introduced into host cells for expressing the kynureninase. The proteins may be expressed in any suitable manner. In one embodiment, the proteins are expressed in a host cell such that the protein is glycosylated. In another embodiment, the proteins are expressed in a host cell such that the protein is aglycosylated.

In some embodiments, the cancer is any cancer that is sensitive to kynurenine depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a kynureninase with kynurenine-degrading activity at physiological conditions and further comprising an attached polyethylene glycol chain. In some embodiment, the formulation is a pharmaceutical formulation comprising any of the above discussed kynureninases and pharmaceutically acceptable excipients. Such pharmaceutically acceptable excipients are well known to those of skill in the art. All of the above kynureninases may be contemplated as useful for human therapy.

In a further embodiment, there may also be provided a method of treating a tumor cell comprising administering a formulation comprising a non-bacterial (mammalian, e.g., primate or mouse) kynureninase that has kynurenine-degrading activity or a nucleic acid encoding thereof.

In accordance with certain aspects of the present invention, such a formulation containing the kynureninase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, intratumorally, intramuscularly, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

In a further embodiment, the method also comprises administering at least a second anticancer therapy to the subject. The second anticancer therapy may be a surgical therapy, chemotherapy, radiation therapy, cryotherapy, hormone therapy, immunotherapy or cytokine therapy. In certain aspects, the second anticancer therapy may be an immune check point inhibitor therapy, such as anti-PD-1, anti-CTLA-4, anti-PD-L1 antibody, anti-LAG3, anti-TIM-3, anti-ICOS, anti-CD137, anti-CD40, anti-KIR, anti-CD40L, anti-GITR, or anti-OX40 therapy. In further aspects, the second anticancer therapy may be an antibody therapy, such as with an antibody-drug conjugate. In still further aspects, the second anticancer therapy is an immunotherapy such as administering immune effector cells or an immunogenic composition. For example, the immunogenic composition can comprise cancer cells antigens and, optionally, an adjuvant. In some aspects, immune effector cells can comprise NK-cells, T-cells (e.g., CAR T-cells) or NK/T-cells.

In some embodiments, a T cell comprising a chimeric antigen receptor (CAR) and a kynureninase enzyme of the embodiments are contemplated for use in treating a subject with cancer. In some aspects, the cell may be transfected with a DNA encoding the CAR and the kynureninase and, in some cases, a transposase.

The CAR may target any cancer-cell antigen of interest, including, for example, HER2, CD19, CD20, and GD2. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, which is incorporated herein by reference in its entirety. The fragment can also be any number of different antigen binding domains of a human antigen-specific antibody. In a more specific embodiment, the fragment is an antigen-specific scFv encoded by a sequence that is optimized for human codon usage for expression in human cells. For additional examples of CARs, see, for example, WO 2012/031744, WO 2012/079000, WO 2013/059593, and U.S. Pat. No. 8,465,743, all of which are incorporated herein by reference in their entireties.

The kynureninase may be any kynureninase disclosed herein. Methods of transfecting of cells are well known in the art, but in certain aspects, highly efficient transfections methods such as electroporation are employed. For example, nucleic acids may be introduced into cells using a nucleofection apparatus. Preferably, the transfection step does not involve infecting or transducing the cells with virus, which can cause genotoxicity and/or lead to an immune response to cells containing viral sequences in a treated subject.

A wide range of CAR constructs and expression vectors for the same are known in the art and are further detailed herein. For example, in some aspects, the CAR expression vector is a DNA expression vector such as a plasmid, linear expression vector or an episome. In some aspects, the vector comprises additional sequences, such as sequence that facilitates expression of the CAR, such a promoter, enhancer, poly-A signal, and/or one or more introns. In preferred aspects, the CAR coding sequence is flanked by transposon sequences, such that the presence of a transposase allows the coding sequence to integrate into the genome of the transfected cell.

In certain aspects, cells are further transfected with a transposase that facilitates integration of a CAR coding sequence into the genome of the transfected cells. In some aspects, the transposase is provided as DNA expression vector. However, in preferred aspects, the transposase is provided as an expressible RNA or a protein such that long-term expression of the transposase does not occur in the transgenic cells. Any transposase system may be used in accordance with the embodiments. In other aspects, cells may be infected with a lentivirus to facilitate integration of the CAR coding sequence and the kynureninase coding sequence into the genome of the cell.

In one embodiment, a composition comprising a kynureninase or a nucleic acid encoding a kynureninase is provided for use in the treatment of a tumor in a subject. In another embodiment, the use of a kynureninase or a nucleic acid encoding a kynureninase in the manufacture of a medicament for the treatment of a tumor is provided. The kynureninase may be any kynureninase of the embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-B: In vivo efficacy of HsKYN variant. A) Protein (68) in combination with antiPD-1 demonstrated significant tumor growth inhibition/survival benefits superior to Epacadostat, in the CT26 model. B) Complete responders (CRs) were re-challenged with CT26 and none of the CRs developed tumors, confirming anti-tumor memory against CT26. In contrast, naive mice inoculated with CT26 developed tumors.

FIGS. 3A-B: Immunoprofiling of Protein (68) in CT26 tumor bearing mice. A) Multiplex gene expression analysis using Nanostring revealed upregulation of IFNγ gene signature upon HsKYN+/−antiPD1 treatment. B) FACs analysis demonstrated that HsKYN treatment increased CD8/Treg and M1/M2 macrophage ratios.

FIGS. 4A-C: The PD/PK profiles of Protein (153) in tox species. A) Protein (153) demonstrated robust and durable plasma Kyn depletion in rats after a single and repeated weekly iv dose(s) of 10 mg/kg. B) Protein (153) degraded plasma Kyn ≥50% for up to 7 days after a single iv dose in cyno monkeys. C) Protein (153) monkey PK profile with a favorable T1/2>6 days.

DESCRIPTION OF ILLUSTRATIVE EMBODIMENTS

I. The Present Embodiments

Figures 1A, 1B, 1C:
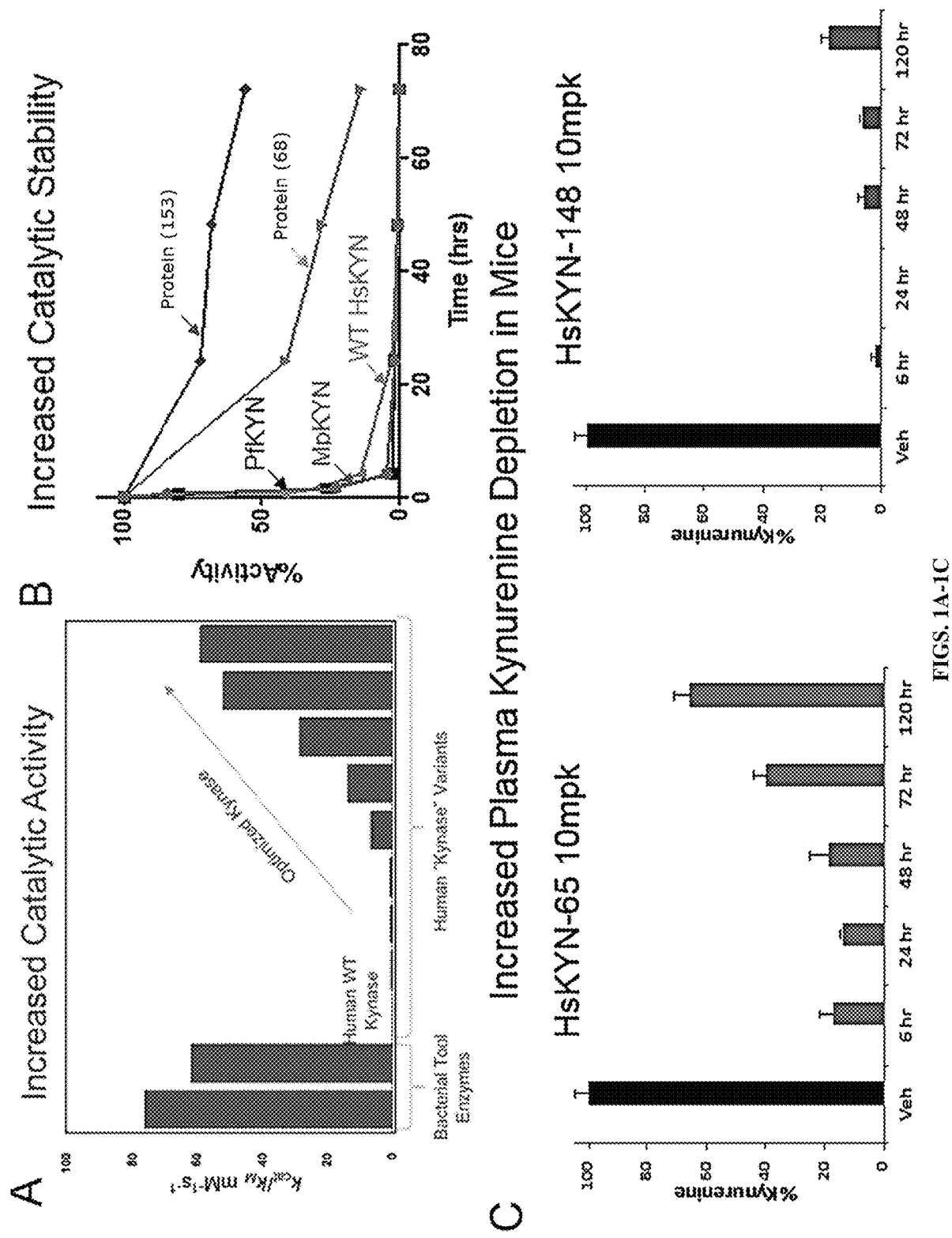
FIGS. 1A-C: Successful outcome of HsKYN protein engineer. A) Human variants achieved >500 fold increase of catalytic activity ($K_{cat}/K_m$) for Kyn, comparable to bacterial tool Kynases. B) Human variants vastly improved catalytic stability in human serum in vitro. C) Human variants (68) and (153), as set forth in Table 1, herein, showed prolonged Kyn degradation in mice after a single iv dose.

In certain embodiments, the present disclosure provides kynureninases (Kynase), a Kyn depleting enzyme. In particular the application provides a set of human kynureninase variants that display at least 100-fold higher catalytic activity towards Kynurenine degradation compared to the wild type human Kynureninase enzyme. In some aspects, kynureninase variants provided herein additionally have increase resistance to deactivation in serum. Thus these enzymes have significantly improved properties that make them ideal for therapeutic disease intervention, such as the treatment of cancer. In some aspects, the enzymes (or sequences encoding the enzymes) can be used to treat cancer patients, such those with IDO1 and/or TDO2 expressing tumors.

In the present studies, the human Kynase (h-KYNase) was been successfully engineered to exhibit vastly improved catalytic activity and stability toward Kyn over the WT enzyme, and achieved durable plasma Kyn depletion in mice. Single agent and PD1 combination efficacy was also demonstrated in CT26 and B16-IDO models, superior to the lead IDO1 inhibitor Epacadostat, and the resulting complete responders (CRs) were resistant to tumor rechallenge. Tumor immunoprofiling revealed upregulation of IFNg signature gene expressions and M1/M2 macrophage ratio upon HsKYN+/−PD1 treatment. The lead HsKYN variant displayed favorable Kyn degradation and PK profile in rats and non-human primates, and may be used for treatment of cancers, such as cancers where IDO1 and/or TDO2 pathways play an immunosuppressive role.

II. Definitions

As used herein the terms "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half-life" (½-life) refers to the time that would be required for the concentration of a polypeptide thereof to fall by half in vitro or in vivo, for example, after injection in a mammal.

The terms "in operable combination," "in operable order," and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term "linker" is meant to refer to a compound or moiety that acts as a molecular bridge to operably link two different molecules, wherein one portion of the linker is operably linked to a first molecule, and wherein another portion of the linker is operably linked to a second molecule.

The term "PEGylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term "gene" refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term "native" refers to the typical form of a gene, a gene product, or a characteristic of that gene or gene product when isolated from a naturally occurring source. A native form is that which is most frequently observed in a natural population and is thus arbitrarily designated the normal or wild-type form. In contrast, the term "modified," "variant," or "mutant" refers to a gene or gene product that displays modification in sequence and functional properties (i.e., altered characteristics) when compared to the native gene or gene product.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "therapeutically effective amount" as used herein refers to an amount of cells and/or therapeutic composition (such as a therapeutic polynucleotide and/or therapeutic polypeptide) that is employed in methods to achieve a therapeutic effect. The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies (such as those described in U.S. Pat. No. 7,109,304, which is incorporated herein by reference in its entirety), fused to CD3-zeta transmembrane and endodomains. The specificity of other CAR designs may be derived from ligands of receptors (e.g., peptides) or from pattern-recognition receptors, such as Dectins. In particular embodiments, one can target malignant B cells by redirecting the specificity of T cells by using a CAR specific for the B-lineage molecule, CD19. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a kynureninase.

"Subject" and "patient" refer to either a human or non-human, such as primates, mammals, and vertebrates. In particular embodiments, the subject is a human.

III. Kynureninase Polypeptides

Some embodiments concern modified proteins and polypeptides. Particular embodiments concern a modified protein or polypeptide that exhibits at least one functional activity that is comparable to the unmodified version, preferably, the kynurenine degrading activity. In further aspects, the protein or polypeptide may be further modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide, such as kynurenine degrading activity or thermodynamic stability.

Determination of activity may be achieved using assays familiar to those of skill in the art, particularly with respect to the protein's activity, and may include for comparison purposes, the use of native and/or recombinant versions of either the modified or unmodified protein or polypeptide.

In certain embodiments, a modified polypeptide, such as a modified kynureninase, may be identified based on its increase in kynurenine. For example, substrate recognition sites of the unmodified polypeptide may be identified. This identification may be based on structural analysis or homology analysis. A population of mutants involving modifications of such substrate recognition sites may be generated. In a further embodiment, mutants with increased kynurenine degrading activity may be selected from the mutant population. Selection of desired mutants may include methods, such as detection of byproducts or products from kynurenine degradation.

Modified proteins may possess deletions and/or substitutions of amino acids; thus, a protein with a deletion, a protein with a substitution, and a protein with a deletion and a substitution are modified proteins. In some embodiments, these modified proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

In certain embodiments, a kynureninase according to the embodiments comprises and amino acid sequence at least about 80%, 85%, 86%, 87%, 88%, 89%, 90%, 91%, 92%, 93%, 94%, 95%, 96%, 97%, 98% or 99% identical to the kynureninase of SEQ ID NOs: 1, 2 or 3. In still further aspects, a kynureninase is at least about 80%, 85%, 86%, 87%, 88%, 89%, 90%, 91%, 92%, 93%, 94%, 95%, 96%, 97%, 98% or 99% identical to the kynureninase of SEQ ID NOs: 1, 2 or 3 and comprises 1, 2, 3, 4, 5, 6, 7, 8, 9, 10, 11, 12, 13, 14, 15, 16, 17, 18, 19, 20, 21, 22, 23, 24 or 25 of the amino acid substitutions selected from the group consisting of L8P, K38E, Y47L, I48F, K50Q, I51M, S60N, K64N, D65G, E66K, N67D, N67P, D67S, A68F, A68T, A68V, F71L, F71M, L72N, K84E, E88N, E89K, E89S, E90Q, D92E, K93N, K93T, A95H, A95Q, K96N, I97H, I97L, I97V, A98G, A99G, A99I, A99R, A99S, A99T, A99V, Y100N, Y100S, Y100T, G101A, H102W, E103F, E103H, E103N, E103Q, E103R, E103V, E103W, V104D, V104E, V104F, V104H, V104K, V104L, V104R, G105A, G105H, G105S, G105T, E106D, K106D, K106E, K106H, K106N, R107P, R107S, P108R, I110A, I110F, I110L, I110M, I110T, T111D, T111H, T111N, T111R, G112A, G112C, G112D, G112K, G112L, G112M, G112Q, G112R, G112S, G112T, G112Y, N127K, I131V, A132V, L133V, A136T, L137T, T138S, N140D, H142Q, Q14R, Y156H, K163T, D168E, H169R, Q175L, I183F, I183L, I183P, I183S, E184A, E184D, E184R, E184T, E184V, E185T, M187L, M189I, K191A, K191G, K191H, K191M, K191N, K191R, K191S, K191T, K191W, E197A, E197D, E197F, E197K, E197M, E197Q, E197S, E197T, E197V, I201C, I201E, I201F, I201H, I201L, I201S, I201T, I201V, H203K, L219M, L219W, F220L, V223I, F225Y, H230F, H230L, H230Y, N232S, Y246F, F249W, D250E, S274A, S274C, S274G, S274N, S274T, L278M, A280G, A280S, A280T, G281S, A282M, A282P, G284N, I285L, V303L, V303S, F306W, F306Y, S31 IN, K315E, D317E, D317K, I331C, I331L, I331N, I331S, I331T, I331V, N333T, P334N, P335T, L337T, L338A, L338Q, S341I, K373E, K373N, N375A, N375H, Y376C, Y376F, Y376L, K378G, K378P, K378Q, K378R, K380G, K380S, A382G, A382R, A382T, T383S, K384G, K384N, P386K, P386S, V387L, N389E, I405L, F407Y, S408D, S408N, N411R, D413S, D413V, Q416T, E419A, E419L, K420E, R421N, V424I, K427M, N429E, G432A and A436T. In further aspects, a kynureninase is at least about 80%, 85%, 86%, 87%, 88%, 89%, 90%, 91%, 92%, 93%, 94%, 95%, 96%, 97%, 98% or 99% identical to one of the kynureninases provided in Table 1. In particular aspects, the kynureninase is selected from one of those provided in Table 1. In some aspects, a kynureninase, e.g., according to Table 1, may or may not be PEGylated.

Table 1, below, sets forth various kynureninase enzymes that may be used in conjunction with the compositions and methods of the present disclosure. Although not listed explicitly in Table 1, "Protein (1)" herein refers to wild-type human kynureninase, the amino acid sequence of which is set forth in SEQ ID NO: 1.

TABLE 1

Exemplary kynureninase enzymes of the embodiments.

| Protein | Number of Mutations | List of Mutations | Tag | PEGylated |
|---|---|---|---|---|
| 2 | 9 | N67D/L72N/E103Q/M189I/F225Y/S274G/I331V/I405L/S408N | His | NO |
| 3 | 9 | N67D/L72N/E103Q/M189I/F225Y/S274G/I331V/I405L/S408N | His | YES |
| 4 | 7 | A99I/G112A/F306Y/I331N/I405L/S408N/A436T | His | NO |
| 5 | 7 | A99I/G112A/F306Y/I331N/I405L/S408N/A436T | His | YES |
| 6 | 10 | Q14R/A99I/G112A/M189I/H230Y/F306Y/I331N/I405L/S408N/A436T | His | NO |
| 7 | 10 | Q14R/A99I/G112A/M189I/H230Y/F306Y/I331N/I405L/S408N/A436T | His | YES |
| 8 | 17 | N67D/L72N/E103Q/A99I/G112A/M189I/F225Y/S274G/I331V/F306Y/K380S/A382R/K384N/P386K/I405L/S408N/A436T | His | NO |
| 9 | 17 | N67D/L72N/E103Q/A99I/G112A/M189I/F225Y/S274G/I331V/F306Y/K380S/A382R/K384N/P386K/I405L/S408N/A436T | His | YES |
| 10 | 18 | N67D/L72N/A99I/H102W/E103F/V104E/K106E/R107S/I110M/A136T/M189I/F225Y/S274G/I331C/N333T/S341I/I405L/S408N | His | NO |
| 11 | 27 | N67D/L72N/A99I/H102W/E103F/V104E/K106E/R107S/I110M/I131V/L133V/A136T/T138S/M189I/F225Y/G274T/L278M/G281S/A282P/F306W/K315E/D317E/I331C/N333T/S341I/I405L/S408N | His | NO |
| 12 | 25 | N67D/L72N/A99I/H102W/E103F/V104E/E106D/R107S/M110I/T111H/G112Y/A132V/A136T/M189I/V223I/F225Y/S274G/A280S/G281S/A282P/I331C/N333T/S341I/I405L/S408N | His | NO |
| 13 | 25 | N67D/L72N/A99I/H102W/E103F/V104E/E106D/R107S/M110I/T111H/G112Y/A132V/A136T/M189I/V223I/F225Y/S274G/A280S/G281S/A282P/I331C/N333T/S341I/I405L/S408N | His | YES |
| 14 | 8 | A99I/G112A/G284N/I285L/F306Y/I331N/I405L/S408N/A436T | His | NO |
| 15 | 7 | A99I/G112A/K191N/F306Y/I331N/I405L/S408N/A436T | His | NO |
| 16 | 10 | L8P/A99I/G112A/Q175L/F306Y/I331N/K373E/K378R/I405L/S408N/A436T | His | NO |
| 17 | 10 | A99I/G112A/F306Y/I331N/K380S/A382R/K384N/P386K/I405L/S408N/A436T | His | NO |
| 18 | 9 | A99I/G112A/F306Y/I331N/N375H/Y376L/K378P/I405L/S408N/A436T | His | NO |
| 19 | 22 | N67D/A68T/L72N/A99I/H102W/E103F/V104E/E106D/R107S/M110I/T111H/G112Y/A136T/M189I/F225Y/S274G/F306W/I331N/N333T/S341I/I405L/S408N | His | NO |
| 20 | 23 | N67D/L72N/A99I/H102W/E103F/V104E/K106E/R107S/I110M/A132V/A136T/M189I/F225Y/G274S/A280S/G281S/A282P/F306W/I331C/N333T/S341I/I405L/S408N | His | NO |
| 21 | 23 | N67D/F71L/L72N/A99I/H102W/E103F/V104E/E106D/R107S/M110I/G112Y/A136T/M189I/F225Y/S274G/A280S/G281S/A282P/I331C/N333T/S341I/I405L/S408N | His | NO |
| 22 | | *sequencing was not fully resolved* | His | NO |
| 23 | 26 | D67N/A68V/L72N/A99I/H102W/E103F/V104E/K106E/R107S/M110I/T111H/G112Y/A136T/M189I/F225Y/G274T/A280S/G281S/A282P/F306W/K315E/I331C/N333T/S341I/I405L/S408N | His | NO |
| 24 | 25 | D67N/L72N/A99I/H102W/E103F/V104E/K106E/R107S/I110M/T111H/G112Y/A136T/M189I/F225Y/G274S/A280S/G281S/A282P/F306W/K315E/I331C/N333T/S341I/I405L/S408N | His | NO |
| 25 | 29 | N67D/L72N/A99I/H102W/E103F/V104E/E106D/R107S/M110I/T111H/G112Y/A132V/A136T/M189I/V223I/F225Y/S274G/A280S/G281S/A282P/V303L/F306W/S311N/K315E/I331C/N333T/S341I/I405L/S408N | His | NO |
| 26 | 23 | D67S/L72N/A99I/H102W/E103F/V104E/K106E/R107S/I110M/A132V/L133V/A136T/M189I/F225Y/G274A/A280S/A282P/F306W/I331C/N333T/S341I/I405L/S408N | His | NO |
| 27 | 24 | D67N/L72N/A99I/H102W/E103F/V104E/K106E/R107S/I110M/T111H/G112Y/A136T/M189I/F225Y/G274N/L278M/A282P/F306W/K315E/I331C/N333T/S341I/I405L/S408N | His | NO |
| 28 | 22 | D67N/A68V/L72N/A99I/H102W/E103F/V104E/K106E/R107S/M110I/A136T/M189I/F225Y/G274T/G281S/A282P/F306W/I331C/N333T/S341I/I405L/S408N | His | NO |
| 29 | 27 | N67D/F71L/L72N/A99I/H102W/E103F/V104E/E106D/R107S/M110I/T111H/G112Y/A136T/M189I/V223I/F225Y/G274S/A280S/G281S/A282P/F306W/K315E/I331C/N333T/S341I/I405L/S408N | His | NO |
| 30 | 25 | D67N/L72N/A99I/H102W/E103F/V104E/K106E/R107S/I110M/T111H/G112Y/A136T/M189I/F225Y/G274S/A280S/G281S/A282P/F306W/D317E/I331C/N333T/S341I/I405L/S408N | His | NO |
| 31 | 29 | N67D/L72N/A99I/H102W/E103F/V104E/E106D/R107S/M110I/T111H/G112Y/A132V/A136T/V223I/M189I/F225Y/S274G/A280S/G281S/A282P/V303S/F306W/K315E/D317K/I331C/N333T/S341I/I405L/S408N | His | NO |
| 32 | 24 | N67D/A68T/L72N/A99I/H102W/E103F/V104E/E106D/R107S/M110I/T111H/G112Y/A136T/M189I/F225Y/G274N/A280S/A282P/F306W/I331C/N333T/S341I/I405L/S408N | His | NO |
| 33 | 24 | N67D/A68T/L72N/A99I/H102W/E103F/V104E/E106D/R107S/M110I/T111H/G112Y/A136T/M189I/F225Y/G274N/A280S/A282P/F306W/I331C/N333T/S341I/I405L/S408N | His | YES |
| 34 | 20 | L72N/A99V/Y100N/H102W/E103F/V104E/K106D/R107S/T111H/G112Y/L133V/A136T/F225Y/S274N/A280S/G281S/A282P/F306W/I331C/N333T | His | NO |

TABLE 1-continued

Exemplary kynureninase enzymes of the embodiments.

| Protein | Number of Mutations | List of Mutations | Tag | PEGylated |
|---|---|---|---|---|
| 35 | 21 | L72N/A99V/Y100N/H102W/E103F/V104E/K106D/R107S/T111N/G112Y/I131V/ L133V/A136T/F225Y/S274T/A280S/G281S/A282P/F306W/I331C/N333T | His | NO |
| 36 | 22 | L72N/A99V/Y100N/H102W/E103F/V104E/K106D/R107S/I110M/T111N/G112Y/ I131V/L133V/A136T/F225Y/S274N/A280S/G281S/A282P/F306W/I331C/N333T | His | NO |
| 37 | 22 | N67D/F71L/L72N/A99V/Y100N/H102W/E103F/V104E/K106D/R107S/I110M/ T111H/G112Y/A136T/F225Y/S274G/A280S/G281S/A282P/F306W/I331C/N333T | His | NO |
| 38 | 21 | L72N/E90Q/A99V/Y100N/H102W/E103F/V104E/K106D/R107S/I110M/T111D/ G112Y/A136T/F225Y/S274N/A280S/G281S/A282M/F306W/I331C/N333T | His | NO |
| 39 | 16 | Y100T/H102W/E103F/V104E/K106D/R107S/T111H/G112Y/A136T/M189I/F225Y/ A280G/A282P/F306W/I331C/N333T | His | NO |
| 40 | 19 | A99S/Y100S/G101A/H102W/E103F/V104E/K106D/R107S/I110M/T111H/G112Y/ A136T/F225Y/A280T/A282P/F306W/I331C/N333T/K373N | His | NO |
| 41 | 3 | K191S-E197T-I201H | His | NO |
| 42 | 3 | K191R-E197S-I201T | His | NO |
| 43 | 3 | K191S-E197T-I201T | His | NO |
| 44 | 2 | I183P-E184A | His | NO |
| 45 | 3 | K191R-E197F-I201T | His | NO |
| 46 | 2 | K191R-I201E | His | NO |
| 47 | 3 | K191W-E197V-I201E | His | NO |
| 48 | 3 | K191H-E197V-I201E | His | NO |
| 49 | 2 | E197M-I201L | His | NO |
| 50 | 3 | K191G-E197V-I201H | His | NO |
| 51 | 3 | K191T-E197Q-I201E | His | NO |
| 52 | 3 | K191H-E197V-I201E | His | NO |
| 53 | 25 | N67D/A68T/L72N/A99I/H102W/E103F/V104E/E106D/R107S/M110I/T111H/G112Y/ A136T/M189I/F225Y/G274N/A280S/A282P/F306W/I331C/N333T/S341I/K373N/ I405L/S408N | His | NO |
| 54 | 22 | L72N/E90Q/A99V/Y100N/H102W/E103F/V104E/K106D/R107S/I110M/T111D/ G112Y/A136T/F225Y/S274N/A280S/G281S/A282M/F306W/I331C/N333T/K373N | His | NO |
| 55 | 37 | N67D/A68T/L72N/E88N/E89K/D92E/K93T/A95Q/K96N/I97H/A98G/A99I/H102W/ E103F/V104E/E106D/R107S/M110L/T111H/G112Y/A136T/M189I/F225Y/A280S/ A282P/F306W/I331L/N333T/P335T/L338A/S341I/I405L/S408N/E419A/K420E/ R421N/V424I | His | NO |
| 56 | 36 (counts deletion of 10 residues as one mutation) | Y47L/I48F/K50Q/del51-62/K64N/D65G/E66K/N67P/A68F/L72N/E88N/E89S/E90Q/K93N/K96N/I97L/A99I/ H102W/E103F/V104E/E106D/R107S/M110L/T111H/G112Y/A136T/M189I/F225Y/ A280G/A282P/F306W/I331C/N333T/S341I/I405L/S408N | His | NO |
| 57 | 29 | Q14R/K38E/I51M/N67D/A68T/L72N/A99I/H102W/E103F/V104E/E106D/R107S/ M110L/T111H/G112Y/N127K/A136T/M189I/K191N/E197T/F225Y/H230F/ S274G/F306W/I331C/N333T/S341I/I405L/S408N | His | NO |
| 58 | 29 | S60N/N67D/L72N/K84E/A99I/H102W/E103F/V104E/E106D/R107S/M110I/T111H/ G112Y/A132V/A136T/Y156H/K163T/M189I/V223I/F225Y/S274G/A280S/G281S/ A282P/I331C/N333T/S341I/I405L/S408N | His | NO |
| 59 | 26 | N67D/L72N/A99I/H102W/E103F/V104E/E106D/R107S/M110I/T111H/G112Y/ A132V/A136T/M189I/V223I/F225Y/S274G/A280S/G281S/A282P/I331C/ N333T/L338Q/S341I/I405L/S408N | His | NO |
| 60 | 26 | N67D/L72N/A99I/Y100N/H102W/E103F/V104E/E106D/R107S/M110I/T111H/ G112Y/A132V/A136T/M189I/V223I/F225Y/S274G/A280S/G281S/A282P/ I331C/N333T/S341I/I405L/S408N | His | NO |
| 61 | 27 | N67D/L72N/I97V/A99I/H102W/E103F/V104E/E106D/R107S/M110I/T111H/G112Y/ A132V/A136T/N140D/M189I/V223I/F225Y/S274G/A280S/G281S/A282P/I331C/ N333T/S341I/I405L/S408N | His | NO |
| 62 | 28 | N67D/A68T/L72N/E90Q/K93N/A95H/K96N/I97L/A99I/H102W/E103F/V104E/ E106D/R107S/M110L/T111H/G112Y/A136T/M189I/F225Y/A280S/A282P/F306W/ I331C/N333T/S341I/I405L/S408N | His | NO |
| 63 | 25 | N67D/L72N/A99I/H102W/E103F/V104E/E106D/R107S/M110I/T111H/G112Y/ A132V/A136T/M189I/V223I/F225Y/S274G/A280S/G281S/A282P/I331C/N333T/ S341I/I405L/S408N | His | NO |
| 64 | 26 | N67D/L72N/A99I/H102W/E103F/V104E/E106D/R107S/M110I/T111H/G112Y/ A132V/A136T/D168E/M189I/V223I/F225Y/S274G/A280S/G281S/A282P/I331C/ N333T/S341I/I405L/S408N | His | NO |
| 65 | 26 | N67D/L72N/A99I/H102W/E103F/V104E/E106D/R107S/M110I/T111H/G112Y/ A132V/A136T/M189I/V223I/F225Y/D250E/S274G/A280S/G281S/A282P/I331C/ N333T/S341I/I405L/S408N | His | NO |
| 66 | 25 | N67D/A68T/L72N/A99I/H102W/E103F/V104E/E106D/R107S/M110I/T111H/ G112Y/A136T/D168E/M189I/F225Y/G274N/A280S/A282P/F306W/I331C/ N333T/S341I/I405L/S408N | His | NO |
| 67 | 25 | N67D/A68T/L72N/A99I/H102W/E103F/V104E/E106D/R107S/M110I/T111H/ G112Y/A136T/M189I/F225Y/D250E/G274N/A280S/A282P/F306W/I331C/ N333T/S341I/I405L/S408N | His | NO |
| 68 | 8 | L72N/A99I/H102W/G112Y/A282P/F306W/I331S/N333T | His | NO |
| 69 | 8 | L72N/A99I/H102W/G112Y/A282P/F306W/I331S/N333T | His | YES |
| 70 | 9 | L72N/A99I/H102W/G112Y/A282P/F306W/I331S/N333T/P334N | His | NO |

TABLE 1-continued

Exemplary kynureninase enzymes of the embodiments.

| Protein | Number of Mutations | List of Mutations | Tag | PEGylated |
|---|---|---|---|---|
| 71 | 16 | L72N/A99I/H102W/E103F/E106D/M110I/T111H/G112Y/A132V/A136T/M189I/A282P/I331C/N333T/S341I/S408N | His | NO |
| 72 | 19 | N67D/L72N/A99I/H102W/E103F/V104E/E106D/R107S/T111H/G112Y/A136T/M189I/A280S/A282P/F306W/I331C/N333T/I405L/S408N | His | NO |
| 73 | 28 | N67D/L72N/A99I/H102W/E103F/V104E/E106D/R107S/M110I/T111H/G112Y/A132V/A136T/M189I/K191S/E197T/I201H/V223I/F225Y/S274G/A280S/G281S/A282P/I331C/N333T/S341I/I405L/S408N | His | NO |
| 74 | 28 | N67D/L72N/A99I/H102W/E103F/V104E/E106D/R107S/M110I/T111H/G112Y/A132V/A136T/M189I/K191R/E197F/I201T/V223I/F225Y/S274G/A280S/G281S/A282P/I331C/N333T/S341I/I405L/S408N | His | NO |
| 75 | 28 | N67D/L72N/A99I/H102W/E103F/V104E/E106D/R107S/M110I/T111H/G112Y/A132V/A136T/M189I/K191SW/E197V/I201E/V223I/F225Y/S274G/A280S/G281S/A282P/I331C/N333T/S341I/I405L/S408N | His | NO |
| 76 | 27 | N67D/L72N/A99I/H102W/E103F/V104E/E106D/R107S/M110I/T111H/G112Y/A132V/A136T/M189I/E197M/I201L/V223I/F225Y/S274G/A280S/G281S/A282P/I331C/N333T/S341I/I405L/S408N | His | NO |
| 77 | 28 | N67D/L72N/A99I/H102W/E103F/V104E/E106D/R107S/M110I/T111H/G112Y/A132V/A136T/M189I/K191H/E197V/I201E/V223I/F225Y/S274G/A280S/G281S/A282P/I331C/N333T/S341I/I405L/S408N | His | NO |
| 78 | 28 | N67D/L72N/A99I/H102W/E103F/V104E/E106D/R107S/M110I/T111H/G112Y/A132V/A136T/M189I/K191R/E197S/I201T/V223I/F225Y/S274G/A280S/G281S/A282P/I331C/N333T/S341I/I405L/S408N | His | NO |
| 79 | 28 | N67D/L72N/A99I/H102W/E103F/V104E/E106D/R107S/M110I/T111H/G112Y/A132V/A136T/M189I/K191G/E197V/I201H/V223I/F225Y/S274G/A280S/G281S/A282P/I331C/N333T/S341I/I405L/S408N | His | NO |
| 80 | 28 | N67D/L72N/A99I/H102W/E103F/V104E/E106D/R107S/M110I/T111H/G112Y/A132V/A136T/M189I/K191S/E197T/I201T/V223I/F225Y/S274G/A280S/G281S/A282P/I331C/N333T/S341I/I405L/S408N | His | NO |
| 81 | 28 | N67D/L72N/A99I/H102W/E103F/V104E/E106D/R107S/M110I/T111H/G112Y/A132V/A136T/M189I/K191G/E197A/I201E/V223I/F225Y/S274G/A280S/G281S/A282P/I331C/N333T/S341I/I405L/S408N | His | NO |
| 82 | 12 | L72N/A99S/H102W/E103F/V104K/K106H/R107S/G112Y/A282P/F306W/I331C/N333T | His | NO |
| 83 | 12 | N67D/L72N/A99I/H102W/K106D/S274G/A280S/G281S/A282P/F306W/I331S/N333T | His | NO |
| 84 | 24 | N67D/A68T/L72N/A99I/H102W/E103F/V104E/K106D/R107S/I110L/T111H/G112Y/A136T/M189I/F225Y/S274N/A280S/A282P/F306W/I331C/N333T/S341I/I405L/S408N | His | NO |
| 85 | 13 | L72N/A99I/H102W/E103V/V104E/K106D/R107S/T111H/G112Y/A282P/F306W/I331S/N333T | His | NO |
| 86 | 12 | L72N/A99V/H102W/E103F/V104E/K106N/T111N/A280S/A282P/F306W/I331S/N333T | His | NO |
| 87 | 10 | L72N/A99I/H102W/G112Y/A282P/F306W/I331S/N333T/T383S/D413V | His | NO |
| 88 | 13 | L72N/A99I/Y100N/H102W/G112Y/H169R/M187L/Y246F/A282P/F306W/I331S/N333T/A382T | His | NO |
| 89 | 11 | L72N/A99I/H102W/V104R/G105H/R107P/G112Y/A282P/F306W/I331S/N333T | His | NO |
| 90 | 11 | L72N/H102W/E103N/K106D/R107P/T111R/G112Y/A282P/F306W/I331T/N333T | His | NO |
| 91 | 10 | L72N/A99I/H102W/G112Y/A282P/F306W/I331S/N333T/Y376F/K378Q | His | NO |
| 92 | 11 | L72N/A99I/H102W/G112Y/K191S/E197D/I201E/A282P/F306W/I331S/N333T | His | NO |
| 93 | 10 | L72N/A99I/H102W/G112Y/K191A/I201V/A282P/F306W/I331S/N333T | His | NO |
| 94 | 15 | L72N/A99I/H102W/G112Y/I183P/E184A/M187L/M189I/K191N/E197T/I201T/A282P/F306W/I331S/N333T | His | NO |
| 95 |  |  | His | NO |
| 96 | 15 | F71M/L72N/E103F/V104H/G105T/I183P/E184A/M187L/M189I/K191N/E197T/I201T/A280S/A282P/F306Y | His | NO |
| 97 | 15 | F71M/L72N/E103F/V104H/G105T/I183P/E184A/M187L/M189I/K191N/E197T/I201T/A280S/A282P/F306Y | His | YES |
| 98 | 7 | L72N/H102W/G112Y/A282P/F306W/I331S/N333T | His | NO |
| 99 | 9 | L72N/G101A/H102W/G112Y/E184A/A282P/F306W/I331S/N333T | His | NO |
| 100 | 10 | L72N/A99I/H102W/G112Y/I183P/E184A/A282P/F306W/I331S/N333T | His | NO |
| 101 | 12 | L72N/A99I/H102W/G112Y/I183L/M189I/K191S/I201T/A282P/F306W/I331S/N333T | His | NO |
| 102 | 12 | L72N/A99I/H102W/G112Y/M187L/M189I/K191R/I201T/A282P/F306W/I331S/N333T | His | NO |
| 103 | 13 | L72N/A99V/E103Q/H102W/G112Y/I183P/E184A/E197A/I201T/A282P/F306W/I331S/N333T | His | NO |
| 104 | 13 | L72N/A99I/H102W/E103Q/V104D/G105S/G112Y/I183P/E184A/A282P/F306W/I331S/N333T | His | NO |
| 105 | 9 | L72N/A99I/H102W/G112Y/I183P/A282P/F306W/I331S/N333T | His | NO |
| 106 | 13 | L72N/A99V/H102W/E103Q/V104H/G112Y/I183P/M189I/K191S/A282P/F306W/I331S/N333T | His | NO |
| 107 | 11 | L72N/H102W/R107P/G112Y/I183P/E184A/E197A/A282P/F306W/I331S/N333T | His | NO |
| 108 | 11 | L72N/A99T/H102W/G112Y/I183P/E184A/I201T/A282P/F306W/I331S/N333T | His | NO |
| 109 | 12 | L72N/A99I/H102W/G112Y/A136T/L137T/F225Y/A282P/F306W/I331S/N333T/F407Y | His | NO |

TABLE 1-continued

Exemplary kynureninase enzymes of the embodiments.

| Protein | Number of Mutations | List of Mutations | Tag | PEGylated |
|---|---|---|---|---|
| 110 | 10 | L72N/A99I/H102W/G112Y/A282P/F306W/I331S/N333T/I405L/S408D/A436T | His | NO |
| 111 | 13 | L72N/A99I/H102W/G112Y/I183P/E184A/M187L/M189I/K191N/A282P/F306W/I331S/N333T | His | NO |
| 112 | 13 | L72N/A99V/H102W/E103Q/G112Y/I183P/E184A/E197A/I201T/A282P/F306W/I331S/N333T | His | NO |
| 113 | 15 | L72N/A99V/H102W/E103Q/V104H/G105A/R107P/G112Y/M187L/K191S/I201T/A282P/F306W/I331S/N333T | His | NO |
| 114 | 15 | L72N/A99V/H102W/E103Q/V104H/G105A/R107P/G112Y/M187L/K191S/I201T/A282P/F306W/I331S/N333T | His | YES |
| 115 | 14 | L72N/H102W/V104D/G105A/G112Y/I183F/E184T/M189I/K191S/I201T/A282P/F306W/I331S/N333T | His | NO |
| 116 | 14 | L72N/A99V/H102W/V104H/G105A/G112Y/M187L/M189I/K191S/I201T/A282P/F306W/I331S/N333T | His | NO |
| 117 | 14 | L72N/A99I/H102W/V104D/G105S/G112Y/I183P/M187L/M189I/I201T/A282P/F306W/I331S/N333T | His | NO |
| 118 | 16 | L72N/A99V/H102W/E103Q/V104D/G112Y/I183P/E184A/M189I/K191R/I201T/A280S/A282P/F306W/I331S/N333T | His | NO |
| 119 | 12 | L72N/A99I/H102W/E103Q/V104H/G112Y/I183L/M189I/A282P/F306W/I331S/N333T | His | NO |
| 120 | 13 | L72N/A99I/H102W/G112Y/I183S/E183A/M189I/K191N/I201T/A282P/F306W/I331S/N333T | His | NO |
| 121 | 10 | L72N/A99I/H102W/G112Y/A136T/L137T/A282P/F306W/I331S/N333T | His | NO |
| 122 | 13 | L72N/A99I/H102W/G112Y/A136T/L137T/F220L/F225Y/H230L/A282P/F306W/I331S/N333T | His | NO |
| 123 | 11 | L72N/A99I/H102W/G112Y/L137T/F220L/H203K/A282P/F306W/I331S/N333T | His | NO |
| 124 | 13 | L72N/A99I/H102W/G112Y/A136T/L137T/F225Y/A282P/F306W/I331S/N333T/F407Y | His | NO |
| 125 | 11 | L72N/A99I/H102W/R107P/G112Y/I183L/E184A/A282P/F306W/I331S/N333T | His | NO |
| 126 | 15 | L72N/A99V/H102W/E103Q/V104H/G105S/R107P/G112Y/M187L/K191R/I201T/A282P/F306W/I331S/N333T | His | NO |
| 127 | 15 | L72N/A99I/H102W/G112Y/I183L/E184R/M187L/M189I/K191N/E197K/I201T/A282P/F306W/I331S/N333T | His | NO |
| 128 | 13 | L72N/A99I/H102W/G112Y/E184D/M187L/M189I/K191R/E197A/I201T/A282P/F306W/I331S/N333T | His | NO |
| 129 | 13 | L72N/A99I/H102W/G112Y/I183S/E184V/M187L/M189I/K191R/A282P/F306W/I331S/N333T | His | NO |
| 130 | 14 | L72N/A99V/H102W/V104D/G112Y/E184A/M187L/M189I/K191R/E197A/A282P/F306W/I331S/N333T | His | NO |
| 131 | 15 | L72N/A99V/H102W/V104H/G105A/G112Y/M189I/K191S/I201T/A282P/F306W/I331S/N333T | His | NO |
| 132 | 16 | L72N/A99I/H102W/E103Q/V104D/G105S/G112Y/I183P/M189I/K191S/I201T/A280S/A282P/F306W/I331S/N333T | His | NO |
| 133 | 13 | L72N/A99V/H102W/E103Q/R107P/G112Y/I183P/E184A/I201T/A282P/F306W/I331S/N333T | His | NO |
| 134 | 14 | L72N/A99T/H102W/E103F/R107P/G112Y/I183P/E184A/I201T/A282P/S724C/F306W/I331S/N333T | His | NO |
| 135 | 9 | L72N/A99V/H102W/R107P/G112Y/A282P/F306W/I331S/N333T | His | NO |
| 136 | 17 | L72N/A99V/H102W/E103Q/V104H/G105A/R107P/G112Y/M187L/K191S/I201T/A282P/F306W/I331S/N333T/I405L/S408D | His | NO |
| 137 | 16 | L72N/A99V/H102W/E103Q/V104D/G112Q/I183P/E184A/M189I/K191R/I201T/A280S/A282P/F306W/I331S/N333T | His | NO |
| 138 | 14 | L72N/A99V/H102W/E103Q/V104H/R107P/G112Y/I183P/A282P/F306W/I331S/N333T/S408N/A436T | His | NO |
| 139 | 17 | L72N/A99V/H102W/E103Q/V104H/G105A/R107P/G112L/M187L/K191S/I201T/F220L/F225Y/A282P/F306W/I331S/N333T | His | NO |
| 140 | 18 | L72N/A99V/H102W/E103Q/V104H/G105A/R107P/G112L/A136T/M187L/K191S/I201T/H230L/A282P/F306W/I331S/N333T | His | NO |
| 141 | 18 | L72N/A99V/H102W/E103Q/V104H/G105A/R107P/G112C/M187L/K191S/I201T/F220L/F225Y/A282P/F306W/I331S/N333T | His | NO |
| 142 | 16 | L72N/A99V/H102W/E103Q/V104D/G112R/I183P/E184A/M189I/K191R/I201T/A280S/A282P/F306W/I331S/N333T | His | NO |
| 143 | 12 | L72N/A99V/H102W/V104H/G105A/M189I/K191S/I201T/A282P/F306W/I331S/N333T | His | NO |
| 144 | 12 | L72N/A99V/H102W/E103Q/V104D/R107P/G112C/I201E/A282P/F306W/I331S/N333T | His | NO |
| 145 | 12 | L72N/A99V/H102W/E103Q/V104D/G112L/M187L/I201T/A282P/F306W/I331S/N333T | His | NO |
| 146 | 12 | L72N/A99V/H102W/E103Q/V104L/G112D/K191S/A282P/F306W/I331S/N333T/S408N | His | NO |
| 147 | 14 | L72N/A99I/H102W/E103Q/V104L/G112Y/A136T/K191S/A282P/F306W/I331S/N333T/S408N/A436T | His | NO |
| 148 | 15 | L72N/A99V/H102W/E103Q/V104L/R107P/G112Y/A136T/I183P/K191S/I201T/A282P/F306W/I331S/N333T | His | NO |
| 149 | 14 | L72N/A99V/H102W/E103Q/V104H/R107P/G112Y/H142Q/K191S/I201T/A282P/F306W/I331S/N333T | His | NO |

TABLE 1-continued

Exemplary kynureninase enzymes of the embodiments.

| Protein | Number of Mutations | List of Mutations | Tag | PEGylated |
|---|---|---|---|---|
| 150 | 14 | L72N/A99I/H102W/E103Q/V104H/G112D/K191S/I201T/F225Y/A282P/F306W/I331S/N333T/S408N | His | NO |
| 151 | 15 | L72N/A99V/H102W/E103Q/V104H/G105A/R107P/G112Y/M187L/K191S/I201T/A282P/F306W/I331S/N333T/S408D | His | NO |
| 152 | 14 | L72N/A99G/H102W/E103H/V104H/R107P/G112Y/I183P/A282P/F306W/I331S/N333T/S408N/A436T | His | NO |
| 153 | 14 | L72N/A99R/H102W/E103R/V104H/R107P/G112Y/I183P/A282P/F306W/I331S/N333T/S408N/A436T | His | NO |
| 154 | 14 | L72N/A99G/H102W/E103W/V104H/R107P/G112Y/I183P/A282P/F306W/I331S/N333T/S408N/A436T | His | NO |
| 155 | 13 | L72N/A99V/H102W/E103Q/V104H/R107P/I183P/A282P/F306W/I331S/N333T/S408N/A436T | His | NO |
| 156 | 15 | L72N/A99V/H102W/E103Q/V104H/R107P/G112Y/N140D/I183P/A282P/F306W/I331S/N333T/S408N/A436T | His | NO |
| 157 | 15 | L72N/A99V/H102W/E103Q/V104H/R107P/I110F/G112Y/I183P/A282P/F306W/I331S/N333T/S408N/A436T | His | NO |
| 158 | 14 | L72N/A99V/H102W/E103Q/V104H/R107P/G112L/I183P/A282P/F306W/I331S/N333T/S408N/A436T | His | NO |
| 159 | 14 | L72N/A99V/H102W/E103Q/V104H/R107P/G112K/I183P/A282P/F306W/I331S/N333T/S408N/A436T | His | NO |
| 160 | 15 | L72N/A99V/H102W/E103Q/V104H/R107P/T111R/G112R/I183P/A282P/F306W/I331S/N333T/S408N/A436T | His | NO |
| 161 | 15 | L72N/A99V/H102W/E103Q/V104H/R107P/G112Y/I183P/L219M/A282P/F306W/I331S/N333T/S408N/A436T | His | NO |
| 162 | 16 | L72N/A99V/H102W/E103Q/V104H/R107P/G105A/R107P/T111N/Y112A/I183P/A282P/F306W/I331S/N333T/S408N/A436T | His | NO |
| 163 | 19 | L72N/A99V/H102W/E103Q/V104H/R107P/G112Y/I183P/E184A/M189I/K191R/I201T/L219W/A282P/F306W/I331S/N333T/S408N/A436T | His | NO |
| 164 | 15 | L72N/A99V/H102W/E103Q/V104H/R107P/G112Y/D168E/I183P/A282P/F306W/I331S/N333T/S408N/A436T | His | NO |
| 165 | 19 | L72N/A99V/H102W/E103Q/V104H/R107P/G112Y/I183P/E184A/M189I/K191R/I201T/F249W/A282P/F306W/I331S/N333T/S408N/A436T | His | NO |
| 166 | 15 | L72N/A99V/H102W/E103Q/V104H/R107P/G112Y/I183P/F249W/A282P/F306W/I331S/N333T/S408N/A436T | His | NO |
| 167 | 14 | Identical AA sequence to (138) | His | NO |
| 168 | 15 | L72N/A99R/H102W/E103R/V104H/R107P/G112Y/I183P/F249W/A282P/F306W/I331S/N333T/S408N/A436T | His | NO |
| 169 | 15 | L72N/A99G/H102W/E103W/V104H/R107P/G112Y/I183P/F249W/A282P/F306W/I331S/N333T/S408N/A436T | His | NO |
| 170 | 15 | L72N/A99G/H102W/E103W/V104H/R107P/Y112K/I183P/F249W/A282P/F306W/I331S/N333T/S408N/A436T | His | NO |
| 171 | 14 | L72N/A99G/H102W/E103W/V104F/R107P/G112Y/I183P/A282P/F306W/I331S/N333T/S408N/A436T | His | NO |
| 172 | 15 | L72N/A99G/H102W/E103W/V104H/R107P/G112Y/I183P/A282P/F306W/I331S/N333T/S408N/A436T AND Arginine Insertion between P107 and P108 | His | NO |
| 173 | 16 | L72N/A99G/H102W/E103W/V104H/R107P/P108R/G112Y/I183P/A282P/F306W/I331S/N333T/S408N/A436T -AND Leucine insertion between P107 and R108 | His | NO |
| 174 | 14 | L72N/A99G/H102W/E103W/V104H/R107P/Y112K/I183P/A282P/F306W/I331S/N333T/S408N/A436T | His | NO |
| 175 | 15 | L72N/A99G/H102W/E103W/V104H/R107P/G112Y/I183P/K191M/A282P/F306W/I331S/N333T/S408N/A436T | His | NO |
| 176 | 17 | L72N/A99G/H102W/E103W/V104H/R107P/G112Y/I183P/M189I/I201S/N232S/A282P/F306W/I331S/N333T/S408N/A436T | His | NO |
| 177 | 18 | L72N/A99G/H102W/E103W/V104H/R107P/G112Y/I183P/E184A/M189I/K191R/I201F/A282P/F306W/I331S/N333T/S408N/A436T | His | NO |
| 178 | 17 | F71M/L72N/E103F/V104H/G105T/I110T/G112T/I183P/E184A/M187L/M189I/K191S/E197T/I201T/A280S/A282P/F306Y | His | NO |
| 179 | 22 | I183P/E184A/M187L/M189I/K191S/E197T/I201T/N375A/Y376C/K378G/K380G/A382G/K384P/P386S/N411R/D413S/Q416T/E419L/K427M/N429E/G432A/A436T | His | NO |
| 180 | 19 | A99I/G112S/F306Y/I405L/S408N/A436T/I183P/E185T/M189I/K191N/N375H/Y376L/K378P/K380S/A382R/K384P/P386K/V387L/N389E | His | NO |
| 181 | 13 | L72N/A99R/H102W/E103R/V104D/G112M/I183P/A282P/F306W/I331S/N333T/S408N/A436T | His | NO |
| 182 | 16 | L72N/A99G/H102W/E103W/V104H/R107P/G112M/I183P/I201F/F249W/A282P/F306W/I331S/N333T/S408N/A436T | His | NO |
| 183 | 17 | L72N/A99G/H102W/E103W/V104H/R107P/G112Y/I183P/M189I/I201C/F249W/A282P/F306W/I331S/N333T/S408N/A436T | His | NO |
| 184 | 15 | L72N/A99R/H102W/E103R/V104H/R107P/G112Y/I183P/A282P/F306W/I331S/N333T/L337T/S408N/A436T | His | NO |
| 185 | 17 | L72N/A99R/H102W/E103R/V104H/R107P/I110A/G112Y/I183P/A280G/A282P/F306W/I331S/N333T/L337T/S408N/A436T | His | NO |

IV. Enzymatic Kynurenine Degradation for Therapy

In certain aspects, the polypeptides may be used for the treatment of diseases, including cancers that are sensitive to kynurenine depletion, with enzymes that deplete kynurenine, to prevent tumor-mediated tolerogenic effects and instead mediate tumor-ablating pro-inflammatory responses. In certain aspects, kynureninases are contemplated for use in treating tumors expressing IDO1, IDO2, and/or TDO.

Certain aspects of the present invention provide a modified kynureninase for treating diseases, such as tumors. Particularly, the modified polypeptide may have human polypeptide sequences and thus may prevent allergic reactions in human patients, allow repeated dosing, and increase the therapeutic efficacy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant, myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The kynureninase may be used herein as an antitumor agent in a variety of modalities for depleting kynurenine and/or kynurenine-derived metabolites from tumor tissue, or the circulation of a mammal with cancer, or for depletion of kynurenine where its depletion is considered desirable.

Depletion can be conducted in vivo in the circulation of a mammal, in vitro in cases where kynurenine and/or kynurenine-derived metabolites depletion in tissue culture or other biological mediums is desired, and in ex vivo procedures where biological fluids, cells, or tissues are manipulated outside the body and subsequently returned to the body of the patient mammal. Depletion of kynurenine from circulation, culture media, biological fluids, or cells is conducted to reduce the amount of kynurenine accessible to the material being treated, and therefore comprises contacting the material to be depleted with a kynurenine-depleting amount of the kynureninase under kynurenine-depleting conditions as to degrade the ambient kynurenine in the material being contacted.

The depletion may be directed to the nutrient source for the cells, and not necessarily the cells themselves. Therefore, in an in vivo application, treating a tumor cell includes contacting the nutrient medium for a population of tumor cells with the kynureninase. In this embodiment, the medium may be blood, lymphatic fluid, spinal fluid and the like bodily fluid where kynurenine depletion is desired.

Kynurenine- and/or kynurenine-derived metabolites depletion efficiency can vary widely depending upon the application, and typically depends upon the amount of kynurenine present in the material, the desired rate of depletion, and the tolerance of the material for exposure to kynureninase. Kynurenine and kynurenine metabolite levels in a material, and therefore rates of kynurenine and kynurenine metabolite depletion from the material, can readily be monitored by a variety of chemical and biochemical methods well known in the art.

Exemplary kynurenine-depleting amounts are described further herein, and can range from 0.001 to 100 units (U) of kynureninase, preferably about 0.01 to 10 U, and more preferably about 0.1 to 5 U kyureninase per milliliter (mL) of material to be treated. Typical dosages can be administered based on body weight, and are in the range of about 5-1000 U/kilogram (kg)/day, preferably about 5-100 U/kg/day, more preferably about 10-50 U/kg/day, and more preferably about 20-40 U/kg/day.

Kynurenine-depleting conditions are buffer and temperature conditions compatible with the biological activity of a kynureninase, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In a particular embodiment, the invention contemplates methods of using a kynureninase as an antitumor agent, and therefore comprises contacting a population of tumor cells with a therapeutically effective amount of kynureninase for a time period sufficient to inhibit tumor cell growth.

A therapeutically effective amount of a kynureninase is a predetermined amount calculated to achieve the desired effect, i.e., to deplete kynurenine in the tumor tissue or in a patient's circulation, and thereby mediate a tumor-ablating pro-inflammatory response. Thus, the dosage ranges for the administration of kynureninase of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

The kynureninase can be administered parenterally by injection or by gradual infusion over time. The kynureninase can be administered intravenously, intraperitoneally, orally, intramuscularly, subcutaneously, intracavity, transdermally, dermally, can be delivered by peristaltic means, can be injected directly into the tissue containing the tumor cells, or can be administered by a pump connected to a catheter that may contain a potential biosensor for kynurenine.

The therapeutic compositions containing kynureninase are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of kynureninase and conversely low serum and tissue levels of kynurenine. Alternatively, continuous intravenous infusion sufficient to maintain concentrations in the blood in the ranges specified for in vivo therapies are contemplated.

V. Conjugates

Compositions and methods of the present invention involve modified kynureninases, such as by forming conjugates with heterologous peptide segments or polymers, such as polyethylene glycol. In further aspects, the kynureninases may be linked to PEG to increase the hydrodynamic radius of the enzyme and hence increase the serum persistence. In certain aspects, the disclosed polypeptide may be conjugated to any targeting agent, such as a ligand having the ability to specifically and stably bind to an external receptor or binding site on a tumor cell (U.S. Patent Publ. 2009/0304666).

A. Fusion Proteins

Certain embodiments of the present invention concern fusion proteins. These molecules may have a native or modified kynureninase linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the kynureninase may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. PEGylation

In certain aspects of the invention, methods and compositions related to PEGylation of kynureninase are disclosed. For example, the kynureninase may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

VI. Proteins and Peptides

In certain embodiments, the present invention concerns novel compositions comprising at least one protein or peptide, such as a kynureninase. These peptides may be comprised in a fusion protein or conjugated to an agent as described supra.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VII. Nucleic Acids and Vectors

In certain aspects of the invention, nucleic acid sequences encoding a kynureninase or a fusion protein containing a kynureninase may be disclosed. Depending on which expression system is used, nucleic acid sequences can be selected based on conventional methods. For example, if the kynureninase is derived from human kynureninase and contains multiple codons that are rarely utilized in *E. coli*, then that may interfere with expression. Therefore, the respective genes or variants thereof may be codon optimized for *E. coli* expression. Various vectors may be also used to express the protein of interest. Exemplary vectors include, but are not limited, plasmid vectors, viral vectors, transposon, or liposome-based vectors.

VIII. Host Cells

Host cells may be any that may be transformed to allow the expression and secretion of kynureninase and conjugates thereof. The host cells may be bacteria, mammalian cells, yeast, or filamentous fungi. Various bacteria include *Escherichia* and *Bacillus*. Yeasts belonging to the genera *Saccharomyces*, or *Pichia* would find use as an appropriate

IX. Pharmaceutical Compositions

It is contemplated that the novel kynureninase can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more kynureninase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one kynureninase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition that includes kynureninases, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the kynureninase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

X. Combination Treatments

In certain embodiments, the compositions and methods of the present embodiments involve administration of a kynureninase in combination with a second or additional therapy. Such therapy can be applied in the treatment of any disease that is associated with kynurenine dependency. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a kynureninase and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a kynureninase or an anti-cancer agent), or by exposing the tissue, tumor, and/or cell with two or more distinct compositions or formulations, wherein one composition provides 1) a kynureninase, 2) an anti-cancer agent, or 3) both a kynureninase and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A kynureninase may be administered before, during, after, or in various combinations relative to an anti-cancer treatment. The administrations may be in intervals ranging from concurrently to minutes to days to weeks. In embodiments where the kynureninase is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the kynureninase and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a kynureninase is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

XI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development and Characterization of Human Kynase (h-KYNase)

The present studies involved engineering h-KYNase variants and develop the variants as therapeutics for a wide range of tumors. Numerous human variants were engineered and their catalytic activity ($K_{cat}/K_m$) for Kyn, comparable to bacterial tool Kynases, was determined (FIG. 1A and Table 2, below). The variants were optimized for increased catalytic activity and for resistance to deactivation in 90% human serum in vitro (expressed as residual activity following incubation in serum for a certain time). It was found that the engineered human variants vastly improved catalytic stability in human serum in vitro (FIG. 1B and Table 2).

The human variants, such as proteins (68) and (153), showed prolonged Kyn degradation in mice after a single intravenous dose (FIG. 1C). For these studies BALB/c female mice, 6-8 weeks, weighed approximately 18-20 g, were dosed iv with either vehicle (PBS pH7.4) or 10 mg/kg (68)/(153). At 6, 24, 48, 72 & 120 hrs after dosing, mice were terminally bled (n=4 mice/time point) and the plasma samples were immediately quenched with acid containing Internal Standard (IS) solution and processed for LC/MS analysis of Kynurenine.

TABLE 2

Catalytic activities and serum stability for selected enzyme variants

| Protein | Co-factor | Fold over Wild Type | $k_{cat}$ (s$^{-1}$) | $K_m$ (mM) | $k_{cat}/K_m$ (M$^{-1}$ s$^{-1}$) | Stability in 90% Serum | Average % Stability | | | |
|---|---|---|---|---|---|---|---|---|---|---|
| | | | | | | | 24 hr | 48 hr | 72 hr | 120 hr |
| 2 | PLP | 27 ± 9 | | | | | | | | |
| 3 | PLP | 28 | 0.86 | 0.31 | 2800 | | | | | |
| 4 | PLP | 19 ± 10 | | | | | | | | |
| 5 | PLP | 15 | 0.85 | 0.57 | 1500 | | | | | |
| 6 | PLP | 16 ± 6 | | | | | | | | |
| 7 | PLP | 12 | 0.71 | 0.57 | 1246 | | | | | |
| 8 | PLP | 15 ± 5 | | | | | | | | |
| 9 | PLP | 10 | 0.71 | 0.69 | 1023 | | | | | |
| 10 | PLP | 58 ± 12 | | | | | | | | |
| 11 | PLP | 176 | 0.6 | 0.034 | 17647 | | | | | |
| 12 | PLP | 554 | 1.21 | 0.022 | 55367 | | | | | |
| 13 | PLP | 698 | 1.5 | 0.021 | 69775 | | | | | |
| 14 | PLP | 24 | 1 | 0.43 | 2350 | | | | | |
| 15 | PLP | 20 | 1.22 | 0.67 | 1967 | | | | | |
| 16 | PLP | 29 | 1.4 | 0.48 | 2920 | | | | | |
| 17 | PLP | 23 | 1.68 | 0.75 | 2250 | | | | | |
| 18 | PLP | 20 | 1.38 | 0.7 | 2000 | | | | | |
| 19 | PLP | 587 | 0.55 | 0.0093 | 58700 | | | | | |
| 20 | PLP | 388 | 0.993 | 0.026 | 38789 | | | | | |
| 21 | PLP | 424 | 0.94 | 0.022 | 42398 | | | | | |
| 22 | PLP | 342 | 1.06 | 0.031 | 34226 | | | | | |
| 23 | PLP | 405 | 0.85 | 0.021 | 40524 | | | | | |
| 24 | PLP | 379 | 0.87 | 0.023 | 37913 | | | | | |
| 25 | PLP | 336 | 0.7 | 0.021 | 33623 | | | | | |
| 26 | PLP | 389 | 0.65 | 0.017 | 38916 | | | | | |
| 27 | PLP | 368 | 0.76 | 0.021 | 36829 | | | | | |
| 28 | PLP | 305 | 1.109 | 0.036 | 30467 | | | | | |
| 29 | PLP | 526 | 1.32 | 0.0251 | 52590 | | | | | |
| 30 | PLP | 342 | 1.06 | 0.031 | 34226 | | | | | |
| 31 | PLP | 277 | 0.698 | 0.0252 | 27698 | | | | | |
| 32 | PLP | 550 | 0.852 | 0.0155 | 54968 | | | | | |
| 33 | PLP | 580 | 1.3 | 0.022 | 57979 | | | | | |
| 34 | PLP | 366 | 1.011 | 0.0276 | 36630 | | | | | |
| 35 | PLP | 219 | 0.874 | 0.0399 | 21904 | | | | | |
| 36 | PLP | 270 | 0.645 | 0.0239 | 26987 | | | | | |
| 37 | PLP | 536 | 0.638 | 0.0119 | 53613 | | | | | |
| 38 | PLP | 488 | 0.84 | 0.0173 | 48790 | | | | | |
| 39 | PLP | 90 | 0.53 | 0.06 | 9020 | | | | | |
| 40 | PLP | 24 | 0.22 | 0.09 | 2400 | | | | | |
| 41 | PLP | 2.1 | 0.50 | 1.90 | 260 | | | | | |
| 42 | PLP | 4 | 0.250 | 0.640 | 400 | | | | | |
| 43 | PLP | 4 | 0.30 | 0.70 | 428 | | | | | |
| 44 | PLP | 3 | 0.15 | 0.48 | 313 | | | | | |
| 45 | PLP | 3 | 0.270 | 0.950 | 280 | | | | | |
| 46 | PLP | 3 | 0.250 | 1.000 | 250 | | | | | |
| 47 | PLP | 3 | 0.250 | 0.730 | 335 | | | | | |
| 48 | PLP | 3 | 0.320 | 0.950 | 340 | | | | | |
| 49 | PLP | 3 | 0.27 | 0.8 | 340 | | | | | |
| 50 | PLP | 3 | 0.23 | 0.7 | 320 | | | | | |
| 51 | PLP | | | | | | | | | |
| 52 | PLP | | | | | | | | | |
| 53 | PLP | 591 | 0.975 | 0.017 | 59075 | | | | | |
| 54 | PLP | 457 | 1.737 | 0.038 | 45706 | | | | | |
| 55 | PLP | 512 | 1.024 | 0.020 | 51222 | | | | | |
| 56 | PLP | 269 | 1.042 | 0.039 | 26861 | | | | | |
| 57 | PLP | 363 | 0.970 | 0.027 | 36330 | | | | | |

TABLE 2-continued

Catalytic activities and serum stability for selected enzyme variants

| Protein | Co-factor | Fold over Wild Type | $k_{cat}$ (s$^{-1}$) | $K_m$ (mM) | $k_{cat}/K_m$ (M$^{-1}$ s$^{-1}$) | Stability in 90% Serum | Average % Stability | | | |
|---|---|---|---|---|---|---|---|---|---|---|
| | | | | | | | 24 hr | 48 hr | 72 hr | 120 hr |
| 58 | PLP | 411 | 1.192 | 0.029 | 41111 | | | | | |
| 59 | PLP | 635 | 1.098 | 0.017 | 63492 | | | | | |
| 60 | PLP | 788 | 1.048 | 0.013 | 78780 | | | | | |
| 61 | PLP | 368 | 0.805 | 0.022 | 36770 | | | | | |
| 62 | PLP | 359 | 0.507 | 0.014 | 35933 | | | | | |
| 63 | PLP | 415 | 0.954 | 0.023 | 41464 | | | | | |
| 64 | PLP | 502 | 0.457 | 0.009 | 50183 | | | | | |
| 65 | PLP | 100 | 0.262 | 0.026 | 10046 | | | | | |
| 66 | PLP | 127 | 0.253 | 0.020 | 12666 | | | | | |
| 67 | PLP | 47 | 0.210 | 0.044 | 4729 | | | | | |
| 68 | PLP | 96 | 0.471 | 0.049 | 9554 | | 41 ± 11 | 28 ± 8 | 14 ± 2 | |
| 69 | PLP | 127 | 0.580 | 0.045 | 12692 | | | | | |
| 70 | PLP | 70 | 0.470 | 0.067 | 7015 | | | | | |
| 71 | PLP | | 0.94 | 0.089 | 10506 | | | | | |
| 72 | PLP | | 2.15 | 0.14 | 15357 | | | | | |
| 73 | PLP | 242 | 1.7 | 70 | 24200 | | | | | |
| 74 | PLP | | | | | | | | | |
| 75 | PLP | | | | | | | | | |
| 76 | PLP | | | | | | | | | |
| 77 | PLP | | | | | | | | | |
| 78 | PLP | | | | | | | | | |
| 79 | PLP | | | | | | | | | |
| 80 | PLP | | | | | | | | | |
| 81 | PLP | | | | | | | | | |
| 82 | PLP | 110 | 0.87 | 0.0787 | 11054.63787 | | | | | |
| 83 | PLP | 159 | 1.27 | 0.08 | 15875 | | | | | |
| 84 | PLP | 292 | 1.75 | 0.06 | 29167 | | | | | |
| 85 | PLP | 85 | 1.27 | 0.15 | 8467 | | | | | |
| 86 | PLP | 149 | 1.28 | 0.086 | 14884 | | | | | |
| 87 | PLP | 100 | 0.712 | 0.071 | 10028 | | | | | |
| 88 | PLP | 63 | 0.95 | 0.15 | 6333 | | | | | |
| 89 | PLP | 138 | 1.38 | 0.1 | 13800 | | | | | |
| 90 | PLP | 120 | 1.2 | 0.1 | 12000 | | | | | |
| 91 | PLP | 141 | 0.82 | 0.058 | 14137.93103 | | | | | |
| 92 | PLP | 90 | 0.72 | 0.08 | 9000 | | | | | |
| 93 | PLP | 83 | 1 | 0.12 | 8333 | | | | | |
| 94 | PLP | 200 | 1.2 | 0.06 | 20000 | | | | | |
| 95 | PLP | | | | | | | | | |
| 96 | PLP | 137 | 1.5 | 0.1 | 13700 | | | | | |
| 97 | PLP | 67 | 0.67 | 0.099 | 6729 | | | | | |
| 98 | PLP | | 0.58 | 0.118 | 4897 | | | | | |
| 99 | PLP | | 0.73 | 0.089 | 8266 | | | | | |
| 100 | PLP | | 0.73 | 0.046 | 16148 | | | | | |
| 101 | PLP | | 1.02 | 0.055 | 18569 | | | | | |
| 102 | PLP | | 0.97 | 0.087 | 11141 | | | | | |
| 103 | PLP | | 0.92 | 0.041 | 22282 | | | | | |
| 104 | PLP | | 0.96 | 0.049 | 19537 | | | | | |
| 105 | PLP | | 1.01 | 0.053 | 18825 | | | | | |
| 106 | PLP | 145 | 0.93 | 0.065 | 14470 | | | | | |
| 107 | PLP | | 0.71 | 0.037 | 19165 | | | | | |
| 108 | PLP | | 0.47 | 0.119 | 3981 | | | | | |
| 109 | PLP | | 0.81 | 0.029 | 27722 | | | | | |
| 110 | PLP | | 0.99 | 0.039 | 25306 | | | | | |
| 111 | PLP | 135.1 | 1.18 | 0.09 | 13511 | | | | | |
| 112 | PLP | 140.2 | 0.76 | 0.05 | 14016 | | | | | |
| 113 | PLP | 248 | 1.44 | 0.06 | 24798 | | 9 | | 3 | |
| 114 | PLP | 271.7 | 0.89 | 0.032 | 27169 | | | | | |
| 115 | PLP | 68.8 | 0.67 | 0.1 | 6883 | | | | | |
| 116 | PLP | 173.3 | 1 | 0.06 | 17326 | | | | | |
| 117 | PLP | 132.3 | 0.99 | 0.08 | 13228 | | | | | |
| 118 | PLP | 193.3 | 1.11 | 0.06 | 19332 | | 16 | | 4 | |
| 119 | PLP | 142 | 1.31 | 0.092 | 14205 | | | | | |
| 120 | PLP | 108 | 0.81 | 0.075 | 10814 | | | | | |
| 121 | PLP | 197 | 0.42 | 0.021 | 19719 | | | | | |
| 122 | PLP | 348 | 0.82 | 0.024 | 34797 | | | | | |
| 123 | PLP | 81 | 1.03 | 0.127 | 8106 | | | | | |
| 124 | PLP | 244 | 0.66 | 0.027 | 24395 | | | | | |
| 125 | PLP | 301 | 1.31 | 0.044 | 30103 | | | | | |
| 126 | PLP | 220 | 0.98 | 0.045 | 21971 | | | | | |
| 127 | PLP | 315 | 1.26 | 0.040 | 31455 | | | | | |
| 128 | PLP | 267 | 1.07 | 0.040 | 26684 | | | | | |
| 129 | PLP | 193 | 0.86 | 0.045 | 19309 | | | | | |
| 130 | PLP | 169 | 0.58 | 0.034 | 16898 | | | | | |
| 131 | PLP | 309 | 1.10 | 0.036 | 30903 | | | | | |

TABLE 2-continued

Catalytic activities and serum stability for selected enzyme variants

| Protein | Co-factor | Fold over Wild Type | $k_{cat}$ (s$^{-1}$) | $K_m$ (mM) | $k_{cat}/K_m$ (M$^{-1}$ s$^{-1}$) | Stability in 90% Serum | Average % Stability | | | |
|---|---|---|---|---|---|---|---|---|---|---|
| | | | | | | | 24 hr | 48 hr | 72 hr | 120 hr |
| 132 | PLP | 192 | 1.15 | 0.060 | 19201 | | | | | |
| 133 | PLP | 169 | 1.07 | 0.063 | 16870 | | | | | |
| 134 | PLP | 150 | 0.82 | 0.054 | 15035 | | | | | |
| 135 | PLP | 75 | 0.82 | 0.109 | 7487 | | | | | |
| 136 | PLP | 350 | 1.235 | 0.035 | 35286 | | | | | |
| 137 | PLP | 210 | 0.943 | 0.0449 | 21002 | | 4 | 2 | 1 | |
| 138 | PLP | 314 | 1.414 | 0.045 | 31422 | | 45 ± 8 | 27 ± 7 | 22 ± 4 | |
| 139 | PLP | 243 | 1.418 | 0.0583 | 24322 | | | | | |
| 140 | PLP | 181 | 0.91 | 0.05 | 18068 | | | | | |
| 141 | PLP | 160 | 0.97 | 0.06 | 16020 | | | | | |
| 142 | PLP | 165 | 1.10 | 0.07 | 16467.07 | | 33 | 18 | 2 | |
| 143 | PLP | 159 | 1.07 | 0.07 | 15952.38 | | | | | |
| 144 | PLP | 139 | 0.08 | 0.05 | 1400 | | | | | |
| 145 | PLP | 88 | 0.93 | 0.11 | 8837.76 | | | | | |
| 146 | PLP | 106 | 0.74 | 0.07 | 10584 | | | | | |
| 147 | PLP | 127 | 1.09 | 0.09 | 12740 | | | | | |
| 148 | PLP | 144 | 1.06 | 0.07 | 14403.79 | | | | | |
| 149 | PLP | 130 | 1.03 | 0.08 | 13039.09 | | | | | |
| 150 | PLP | 130 | 1.03 | 0.05 | 18889 | | | | | |
| 151 | PLP | 130 | 1.08 | 0.08 | 13626 | | | | | |
| 152 | PLP | 92 | 0.692 | 0.0756 | 9153 | | 62 | 42 | 32 | |
| 153 | PLP | 337 | 1.01 | 0.03 | 33667 | | 72 ± 8 | 68 ± 10 | 56 ± 8 | |
| 154 | PLP | 235 | 0.598 | 0.0255 | 23451 | | 69 | | 53 | |
| 155 | PLP | 236 | 1.21 | 0.051 | 23633 | | 26 | 5 | 0 | |
| 156 | PLP | 353 | 1.15 | 0.033 | 35323 | | 35 | 3 | 0 | |
| 157 | PLP | 423 | 1.26 | 0.030 | 42282 | | 76 | 59 | 38 | |
| 158 | PLP | 309 | 1.14 | 0.037 | 30894 | | 66 | 48 | 33 | |
| 159 | PLP | 296 | 1.39 | 0.047 | 29638 | | 55 | 35 | 22 | |
| 160 | PLP | 243 | 1.98 | 0.081 | 24335 | | 41 | 16 | 3 | |
| 161 | PLP | 251 | 1.05 | 0.042 | 25120 | | 71 | 66 | 55 | |
| 162 | PLP | 248 | 1.12 | 0.045 | 24800 | | 63 | 55 | 41 | |
| 163 | PLP | 173 | 0.99 | 0.058 | 17290 | | 77 | 66 | 45 | |
| 164 | PLP | 330 | 0.34 | 0.010 | 33010 | | 16 | 5 | 0 | |
| 165 | PLP | 354 | 1.63 | 0.046 | 35430 | | 87 | 51 | 42 | |
| 166 | PLP | 347 | 1.06 | 0.031 | 34710 | | 76 | 53 | 43 | |
| 167 | PLP | 316 | 1.04 | 0.033 | 31650 | | 69 | 51 | 45 | |
| 168 | PLP | 330 | 0.78 | 0.024 | 33000 | | 97 ± 1 | 88 ± 11 | 82 ± 1 | |
| 169 | PLP | 99 | 0.47 | 0.047 | 9900 | | 73 | 75 | 56 | |
| 170 | PLP | 177 | 0.70 | 0.040 | 17663.0 | | 76 | 65 | 60 | |
| 171 | PLP | 275 | 0.71 | 0.026 | 27517.0 | | 65 | 63 | 57 | |
| 172 | PLP | 148 | 0.53 | 0.036 | 14750.0 | | 79 | 79 | 65 | |
| 173 | PLP | 209 | 0.99 | 0.047 | 20930.0 | | 83 | 64 | 72 | |
| 174 | PLP | 274 | 0.58 | 0.021 | 27371.0 | | 68 | 76 | 47 | |
| 175 | PLP | 146 | 0.56 | 0.038 | 14605.0 | | 69 | 73 | 65 | |
| 176 | PLP | 206 | 0.60 | 0.029 | 20552.0 | | 64 | 67 | 44 | |
| 177 | PLP | 167 | 0.63 | 0.038 | 16684.0 | | 65 | 45 | 43 | |
| 178 | PLP | 160 | 1.40 | 0.090 | 15500 | | | | | |
| 179 | PLP | 14 | 1.10 | 0.80 | 1400 | | | | | |
| 180 | PLP | 20 | 1.40 | 0.70 | 2000 | | | | | |
| 181 | PLP | 115 | 0.723 | 0.063 | 11476.2 | | 70 | | | 22 |
| 182 | PLP | 171 | 0.685 | 0.040 | 17125.0 | | 52 | | | 25 |
| 183 | PLP | 171 | 0.684 | 0.040 | 17100.0 | | 91 | | | 45 |
| 184 | PLP | 346 | 1.440 | 0.042 | 34615.4 | | 63 | | | 00 |
| 185 | PLP | 137 | 0.959 | 0.070 | 13700.0 | | 0 | | | |

Example 2—HsKYN Efficacy and Anti-Tumor Memory

Next, the in vivo efficacy of the HsKYN variant was tested in the CT26 mouse model as well as B16-IDO models. 6-8 week old female BALB/c mice were implanted subcutaneously with 500,000 CT26 cells in 100 μl PBS into the lower right flank. Dosing commenced on Day 4 after cell inoculation. Protein (68) was dosed subcutaneously at 10 mg/kg Q6D for 3 doses; Epacadostat was dosed orally at 300 mg/kg QD (5 days on 2 days off); AntiPD-1 was dosed intraperitoneally at 10 mg/kg Q3D for 5 doses. Tumors were measured three times a week with digital calipers and tumor volumes were calculated using the formula Volume=(L×W×T)×Pi/6. Animals were sacrificed when tumors reach >2,000 mm$^3$ (FIG. 2A). One hundred days after the appearance of the last complete responder (CR) from (A), naive BALB/c mice and CRs were re-challenged with CT26 implanted subcutaneously into the lower left flank. Tumor volumes were measured as described above and results are shown in FIG. 2B.

Example 3—HsKYN Tumor Immunoprofiling

Immunoprofiling of (68) was performed in CT26 tumor bearing mice. 6-8 week old female BALB/c were implanted subcutaneously with 500,000 CT26 cells in 100 μl PBS into the lower right flank. Dosing commenced on Day 4 after cell inoculation. Tumors were measured three times a week with digital calipers and tumor volumes were calculated using the formula Volume=(L×W×T)×Pi/6. Animals were sacrificed 24 h after the last dose and tumors collected for further analysis. Protein (68) was dosed subcutaneously at 10 mg/kg Q6D for 2 doses; AntiPD-1 was dosed intraperitoneally at 10 mg/kg Q3D for 3 doses. RNA was extracted using Qiagen RNAeasy kit and 100 ng of RNA were used for Nanostring analysis using the PanCancer Immune Profiling Panel (FIG. 3A). For the studies in FIG. 3B, (68) was dosed subcutaneously at 10 mg/kg Q6D for 2 doses. Tumors were digested with the tumor dissociation kit from Miltenyi. Single cell suspensions were stained with labeled antibodies and analyzed using Fortessa: CD8 (CD45+ CD3+ CD8+ CD4−); Tregs (CD45+ CD3+ CD4+ CD8− FoxP3+ CD25+); M1 macrophages (CD45+ CD11b+ F4/80+ MHCII+ CD206−); M2 macrophages (CD45+ CD11b+ F4/80+ MHCII+ CD206+).

Example 4—Lead HsKYN Variant PD and PK Profiles in Rat and NHP

Male Sprague Dawley rats (200-300 g) were dosed iv, with either a single dose or 3 weekly doses of 10 mg/kg (153), by slow injection via tail vein. Blood was collected 24 hrs before dose (−24 h), 6, 24, 48, 72 or 120 hrs after 1st, 2nd or 3rd dose (n=4 mice/time point). Plasma samples were processed as described in FIG. 1C and Kynurenine levels were analyzed by LC/MS (FIG. 4A). Next, one male and one female Cynomolgus monkeys (≥2 years old) were dosed iv with a single dose of 10 mg/kg (153) by slow injection via the cephalic vein. Blood was collected predose (0 h), 0.25, 6, 24, 48, 72, 120, 168, 240 and 336 hrs post dosing. Plasma samples were divided into two parts: one part was processed as described in FIG. 1C for Kynurenine LC/MS analysis (FIG. 4B); the other part was subject to ELISA analysis of pegylated protein (anti-PEG antibody (Abcam #ab51257) capture and biotinylated anti-PEG antibody (Abcam #ab53449) detection). Plasma concentration versus time data were analyzed by non-compartmental approaches using the WinNonlin software program, and pharmacokinetic parameters with C0, Cmax, T1/2, AUCO-last, AUCO-inf were calculated.

Thus, the present studies showed that Kynurenine degradation by Kynase is broadly applicable to both IDO and TDO expressing tumors. HsKYN protein engineering achieved a more than 500-fold increase of catalytic activity, and vastly improved catalytic stability, leading to robust and durable Kyn depletion in vivo. The HsKYN variant demonstrated superior single agent and PD1 combination efficacy as compared to Epacadostat, as well as sustained anti-tumor memory. The increased IFNg related T-cell inflammatory signature gene expression and M1/M2 macrophage ratio are likely the mechanisms underlying HsKYN+/−PD1 mediated tumor efficacy. Finally, the favorable PK/PD profiles in preclinical tox species support further clinical development of the lead HsKYN variant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahmed et al., HER2-specific T cells target primary glioblastoma stem cells and induce regression of autologous experimental tumors. *Clinical Cancer Research*, 16(2): 474-485, 2010.

Austin-Ward and Villaseca, *Revista Medica de Chile*, 126 (7):838-845, 1998.

Ausubel et al., Current Protocols in Molecular Biology, Greene Publishing Associates and Wiley Interscience, N.Y., 1994.

Bukowski et al., *Clinical Cancer Res.*, 4(10):2337-2347, 1998.

Chen and Guillemin, Kynurenine pathway metabolites in humans: disease and healthy States. *Int J Tryptophan Res*, 2:1-19, 2009.

Christodoulides et al., *Microbiology*, 144(Pt 11):3027-3037, 1998.

Cole and Gaucher, Exploiting models of molecular evolution to efficiently direct protein engineering. *J. Mol. Evol.*, 72:193, 2011.

Curran et al., PD-1 and CTLA-4 combination blockade expands infiltrating T cells and reduces regulatory T and myeloid cells within B16 melanoma tumors. *Proceedings of the National Academy of Sciences*, 107:4275-4280, 2010.

Davidson et al., *J. Immunother.*, 21(5):389-398, 1998.

de Jong et al., Serum tryptophan and kynurenine concentrations as parameters for indoleamine 2,3-dioxygenase activity in patients with endometrial, ovarian, and vulvar cancer. *Int J Gynecol Cancer*, 21(7):1320-1327, 2011.

Della Chiesa et al., The tryptophan catabolite L-kynurenine inhibits the surface expression of NKp46- and NKG2D-activating receptors and regulates NK-cell function. *Blood*, 108(13):4118-4125, 2006.

Godin-Ethier et al., Indoleamine 2, 3-Dioxygenase Expression in Human Cancers: Clinical and Immunologic Perspectives. *Clinical Cancer Research*, 17(22):6985-6991, 2011.

Hanibuchi et al., *Int. J. Cancer*, 78(4):480-485, 1998.
Harkki et al., *BioTechnology*, 7:596-603, 1989.
Hellstrand et al., *Acta Oncologica*, 37(4):347-353, 1998.
Hollander, *Front. Immun.*, 3:3, 2012.
Holmgaard et al., Indoleamine 2, 3-dioxygenase is a critical resistance mechanism in antitumor T cell immunotherapy targeting CTLA-4. *The Journal of Experimental Medicine*, 210:1389-1402, 2013.

Hoover and Lubkowski, DNAWorks: an automated method for designing oligonucleotides for PCR-based gene synthesis. *Nucleic Acids Research*, 30(10):e43-e43, 2002.

Hopwood et al., In: *Genetic Manipulation of Streptomyces*, A Laboratory Manual, The John Innes Foundation, Norwich, Conn., 1985.

Hui and Hashimoto, *Infection Immun.*, 66(11):5329-5336, 1998.

Ito et al., *J. Biochem.*, 79:1263, 1976.

Kaper et al., Nanosensor detection of an immunoregulatory tryptophan influx/kynurenine efflux cycle. *PLoS Biology*, 5(10):e257, 2007.

Lipowska-Bhalla et al., Targeted immunotherapy of cancer with CAR T cells: achievements and challenges. *Cancer Immunology Immunotherapy*, 61(7):953-962, 2012.

Lob et al., Inhibitors of indoleamine-2,3-dioxygenase for cancer therapy: can we see the wood for the trees? *Nat Rev Cancer*, 9(6):445-452, 2009.

Lordanescu, *J. Bacteriol*, 12:597 601, 1975.

Mandi and Vecsei, The kynurenine system and immunoregulation. *J Neural Transm*, 119(2):197-209, 2012.

Maniatis, et al., Molecular Cloning, A Laboratory Manual, Cold Spring Harbor Press, Cold Spring Harbor, N.Y., 1988.

Mellor et al., *Gene*, 24:1-14, 1983.

Mezrich et al., An interaction between kynurenine and the aryl hydrocarbon receptor can generate regulatory T cells. *The Journal of Immunology*, 185(6):3190-3198, 2010.

Opitz et al., The Indoleamine-2, 3-Dioxygenase (IDO) Inhibitor 1-Methyl-D-tryptophan Upregulates IDO1 in Human Cancer Cells. *PLoS One*, 6(5):e19823, 2011.

Opitz et al., An endogenous tumour-promoting ligand of the human aryl hydrocarbon receptor. *Nature*, 478(7368): 197-203, 2011.

Penttila et al., *Gene*, 61:155-164, 1987.

Pilotte et al., Reversal of tumoral immune resistance by inhibition of tryptophan 2,3-dioxygenase. *Proc Natl Acad Sci USA*, 109(7):2497-2502, 2012.

Prendergast, Cancer: Why tumours eat tryptophan. *Nature*, 478(7368):192-194, 2011.

Qin et al., *Proc. Natl. Acad. Sci. USA*, 95(24):14411-14416, 1998.

Remington's Pharmaceutical Sciences, 18th Ed. Mack Printing Company, 1289-1329, 1990.

Rutella et al., Targeting indoleamine 2,3-dioxygenase (IDO) to counteract tumour-induced immune dysfunction: from biochemistry to clinical development. *Endocr Metab Immune Disord Drug Targets*, 9(2):151-177, 2009.

Schellenberger et al., *Nature Biotech.*, 27:1186-1190, 2009.

Shin et al., Modulation of natural killer cell antitumor activity by the aryl hydrocarbon receptor. *Proc Natl Acad Sci USA*, 110(30):12391-12396, 2013.

Sibakov et al., *Eur. J. Biochem.*, 145:567 572, 1984.

Song et al., L-Kynurenine-induced apoptosis in human NK cells is mediated by reactive oxygen species. *International Immunopharmacology*, 11(8):932-938, 2011.

Stone el al., Replacing $Mn^{2+}$ with $Co^{2+}$ in human arginase I enhances cytotoxicity toward L-arginine auxotrophic cancer cell lines. *ACS Chemical Biology*, 5:333-342, 2010.

Voigt et al., Protein building blocks preserved by recombination. *Nature Structural & Molecular Biology*, 9:553, 2002.

Ward, Proc, Embo-Alko Workshop on Molecular Biology of Filamentous Fungi, Helsinki, 119-128, 1989.

Wawrzynczak and Thorpe, In: *Immunoconjugates, Antibody Conjugates In Radioimaging And Therapy Of Cancer*, Vogel (Ed.), NY, Oxford University Press, 28, 1987.

Yao et al., Serum metabolic profiling and features of papillary thyroid carcinoma and nodular goiter. *Mol Biosyst*, 7(9):2608-2614, 2011.

Yoshikawa et al., Serum concentration of L-kynurenine predicts the clinical outcome of patients with diffuse large B-cell lymphoma treated with R-CHOP. *Eur J Haematol*, 84(4):304-309, 2010.

The disclosure is further described in the following numbered embodiments:

Embodiment 1. An isolated, modified human kynureninase enzyme, said modified enzyme having an amino acid sequence that is at least 90% identical to a human kynureninase enzyme of SEQ ID NO: 1 and comprising at least one substitution selected from the group consisting of L8P, K38E, Y47L, I48F, K50Q, I51M, S60N, K64N, D65G, E66K, N67D, N67P, D67S, A68F, A68T, A68V, F71L, F71M, L72N, K84E, E88N, E89K, E89S, E90Q, D92E, K93N, K93T, A95H, A95Q, K96N, I97H, I97L, I97V, A98G, A99G, A99I, A99R, A99S, A99T, A99V, Y100N, Y100S, Y100T, G101A, H102W, E103F, E103H, E103N, E103Q, E103R, E103V, E103W, V104D, V104E, V104F, V104H, V104K, V104L, V104R, G105A, G105H, G105S, G105T, E106D, K106D, K106E, K106H, K106N, R107P, R107S, P108R, I110A, I110F, I110L, I110M, I110T, T111D, T111H, T111N, T111R, G112A, G112C, G112D, G112K, G112L, G112M, G112Q, G112R, G112S, G112T, G112Y, N127K, I131V, A132V, L133V, A136T, L137T, T138S, N140D, H142Q, Q14R, Y156H, K163T, D168E, H169R, Q175L, I183P, I183L, I183P, I183S, E184A, E184D, E184R, E184T, E184V, E185T, M187L, M189I, K191A, K191G, K191H, K191M, K191N, K191R, K191S, K191T, K191W, E197A, E197D, E197F, E197K, E197M, E197Q, E197S, E197T, E197V, I201C, I201E, I201F, I201H, I201L, I201S, I201T, I201V, H203K, L219M, L219W, F220L, V223L, F225Y, H230F, H230L, H230Y, N232S, Y246F, F249W, D250E, S274A, S274C, S274G, S274N, S274T, L278M, A280G, A280S, A280T, G281S, A282M, A282P, G284N, I285L, V303L, V303S, F306W, F306Y, S311N, K315E, D317E, D317K, I331C, I331L, I331N, I331S, I331T, I331V, N333T, P334N, P335T, L337T, L338A, L338Q, S341I, K373E, K373N, N375A, N375H, Y376C, Y376F, Y376L, K378G, K378P, K378Q, K378R, K380G, K380S, A382G, A382R, A382T, T383S, K384G, K384N, P386K, P386S, V387L, N389E, I405L, F407Y, S408D, S408N, N411R, D413S, D413V, Q416T, E419A, E419L, K420E, R421N, V424L, K427M, N429E, G432A, and A436T.

Embodiment 2. The enzyme of embodiment 1, wherein the amino acid sequence is at least 90% identical to the amino acid sequence of any one of the polypeptides of Table 1.

Embodiment 3. The enzyme of embodiment 1 or 2, comprising a substitution at A282, F306 and/or F249.

Embodiment 4. The enzyme of any one of embodiments 1-3, comprising the F306W substitution.

Embodiment 5. The enzyme of any one of embodiments 1-4, comprising the L72N substitution.

Embodiment 6. The enzyme of any one of embodiments 1-5, comprising the H102W and/or N333T substitutions.

Embodiment 7. The enzyme of any one of embodiments 1-6, comprising a substitution at A99.

Embodiment 8. The enzyme of any one of embodiments 1-7, comprising a substitution at G112.

Embodiment 9. The enzyme of any one of embodiments 1-8, comprising a substitution at E103.

Embodiment 10. The enzyme of any one of embodiments 1-9, comprising a substitution at V104.

Embodiment 11. The enzyme of any one of embodiments 1-10, comprising a substitution at S408.

Embodiment 12. The enzyme of any one of embodiments 1-11, comprising the I183P substitution.

Embodiment 13. The enzyme of any one of embodiments 1-12, comprising the R107P substitution.

Embodiment 14. The enzyme of any one of embodiments 1-13, comprising the A436T substitution.

Embodiment 15. The enzyme of any one of embodiments 1-14, comprising at least one substitution selected from L72N, H102W, A282P, F306W, I331S and N333T.

Embodiment 16. The enzyme of any one of embodiments 1-15, comprising at least two, three, four or five substitutions selected from L72N, H102W, A282P, F306W, I331S and N333T.

Embodiment 17. The enzyme of any one of embodiments 1-16, comprising the substitutions L72N, H102W, A282P, F306W, I331S and N333T.

Embodiment 18. The enzyme of any one of embodiments 1-17, wherein the enzyme has a catalytic activity relative the KYN (kcat/kM) of at least 8000 $M^{-1}s^{-1}$.

Embodiment 19. The enzyme of any one of embodiments 1-18, wherein the enzyme has a catalytic activity for kynurenine (KYN) (kcat/kM) of between about 8000 $M^{-1}s^{-1}$ and 40000 $M^{-1}s^{-1}$; 10000 $M^{-1}s^{-1}$ and 40000 $M^{-1}s^{-1}$; 20000 $M^{-1}s^{-1}$ and 40000 $M^{-1}s^{-1}$: or 25000 $M^{-1}s^{-1}$ and 35000 $M^{-1}s^{-1}$.

Embodiment 20. The enzyme of any one of embodiments 1-19, wherein the amino acid sequence is at least 90% identical to the amino acid sequence of SEQ ID NO: 2.

Embodiment 21. The enzyme of embodiment 20, wherein the amino acid sequence is at least 95% identical to the amino acid sequence of SEQ ID NO: 2.

Embodiment 22. The enzyme of any one of embodiments 1-19, wherein the amino acid sequence is at least 90% identical to the amino acid sequence of SEQ ID NO: 3.

Embodiment 23. The enzyme of embodiment 22, wherein the amino acid sequence is at least 95% identical to the amino acid sequence of SEQ ID NO: 3.

Embodiment 24. The enzyme of any one of embodiments 1-23, further comprising a heterologous peptide segment.

Embodiment 25. The enzyme of any one of embodiments 1-24, wherein the enzyme is coupled to polyethylene glycol (PEG).

Embodiment 26. The enzyme of embodiment 25, wherein the enzyme is coupled to PEG via one or more Lys or Cys residues.

Embodiment 27. A nucleic acid comprising a nucleotide sequence encoding the enzyme of any one of embodiments 1-26.

Embodiment 28. The nucleic acid of embodiment 27, wherein the nucleic acid is codon optimized for expression in bacteria, fungus, insects, or mammals.

Embodiment 29. An expression vector comprising the nucleic acid of embodiment 27 or 28.

Embodiment 30. A host cell comprising the nucleic acid of embodiment 27 or 28 or the expression vector of embodiment 29.

Embodiment 31. The host cell of embodiment 30, wherein the host cell is a bacterial cell, a fungal cell, an insect cell, or a mammalian cell.

Embodiment 32. The host cell of embodiment 31, wherein the host cell is a bacterial cell.

Embodiment 33. The host cell of embodiment 31, wherein the host cell is a mammalian cell, optionally wherein the mammalian cell is an immune effector cell.

Embodiment 34. The host cell of embodiment 33, wherein the immune effector cell is a NK-cell or a T-cell.

Embodiment 35. A pharmaceutical formulation comprising an enzyme in accordance with any one of embodiments 1-26 in a pharmaceutically acceptable carrier.

Embodiment 36. A method of treating a subject having a tumor comprising administering to the subject an effective amount of the enzyme of any one of embodiments 1-26 or the formulation of embodiment 35.

Embodiment 37. A composition comprising an effective amount of the enzyme of any one of embodiments 1-26 or the formulation of embodiment 35, for use in the treatment a subject having a tumor.

Embodiment 38. The method of embodiment 36 or composition of embodiment 37, wherein the subject has been identified as having an IDO1, IDO2, or TDO-expressing tumor.

Embodiment 39. The method of embodiment 36 or 38, or the composition of embodiment 37 or 38, wherein the tumor is a solid tumor.

Embodiment 40. The method of embodiment 36 or 38, or the composition of embodiment 37 or 38, wherein the tumor is a hematological tumor.

Embodiment 41. The method of any one of embodiments 36 and 38-40, or the composition of any one of embodiments 37-40, wherein the subject is a human patient.

Embodiment 42. The method of any one of embodiments 36 and 38-41, or the composition of any one of embodiments 37-41, wherein the enzyme or formulation is administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage.

Embodiment 43. The method of any one of embodiments 36 and 38-42, further comprising administering at least a second anti-cancer therapy.

Embodiment 44. The method of embodiment 43, wherein the second anticancer therapy is radiation therapy, surgical therapy, an immunotherapy or a second anticancer compound.

Embodiment 45. The method of embodiment 44, wherein the second anticancer compound is an immune checkpoint inhibitor.

Embodiment 46. The method of embodiment 44 or 45, wherein the second anticancer compound is an antibody.

Embodiment 47. The method of any one of embodiments 44-46, wherein the second anticancer compound comprises an anti-PD1, anti-CTLA-4, or anti-PD-L1 antibody.

Embodiment 48. The method of any one of embodiments 44-47, wherein the second anticancer compound is an antibody-drug conjugate.

Embodiment 49. The method of any one of embodiments 44-48, wherein the immunotherapy comprises administering immune effector cells or an immunogenic composition.

Embodiment 50. The method of embodiment 49, wherein the immunogenic composition comprises cancer cell antigens.

Embodiment 51. The method of embodiment 49 or 50, wherein the immune effector cells comprise NK-cells or T-cells.

Embodiment 52. The method of any one of embodiments 49-51, wherein the immune effector cells comprise CAR T-cells.

Embodiment 53. A transgenic T cell comprising an expressed kynureninase enzyme according to any one of embodiments 1-26.

Embodiment 54. The cell of embodiment 53, further comprising an expressed chimeric antigen T-cell receptor (CAR) or an engineered T-cell receptor (TCR).

Embodiment 55. The cell of embodiment 53 or 54, wherein the cell is a human T cell.

Embodiment 56. The cell of embodiment 54 or 55, wherein DNA encoding the CAR and the kynureninase is integrated into the genome of the cell.

Embodiment 57. The cell of any one of embodiments 54-56, wherein the CAR is targeted to a cancer-cell antigen.

Embodiment 58. The cell of embodiment 57, wherein the cancer-cell antigen is HER2, CD19, CD20, or GD2.

Embodiment 59. A method of providing a T-cell response in a human subject having a tumor comprising administering an effective amount of transgenic cells in accordance with any one of embodiments 53-58 to the subject.

Embodiment 60. A composition comprising an effective amount of transgenic cells in accordance with any one of embodiments 53-58, for use in the treatment a subject having a tumor.

Embodiment 61. The method of embodiment 59 or the composition of embodiment 60, wherein the transgenic cells are autologous.

Embodiment 62. The method of embodiment 59 or the composition of embodiment 60, wherein the transgenic cells are heterologous.

Embodiment 63. Use of a kynureninase enzyme in accordance with any one of embodiments 1-26, a nucleic acid in accordance with embodiment 27 or 28, or an expression vector in accordance with embodiment 29, in the manufacture of a medicament for the treatment of a tumor.

```
Sequence appendix:

SEQ ID NO: 1: wild type human KYNase
MEPSSLELPADTVQRIAAELKCHPTDERVALHLDEEDKLRHFRECFYIPKIQDLPPVDLSL
VNKDENAIYFLGNSLGLQPKMVKTYLEEELDKWAKIAAYGHEVGKRPWITGDESIVGL
MKDIVGANEKEIALMNALTVNLHLLMLSFFKPTPKRYKILLEAKAFPSDHYAIESQLQLH
GLNIEESMRMIKPREGEETLRIEDILEVIEKEGDSIAVILFSGVHFYTGQHFNIPAITKAGQ
AKGCYVGFDLAHAVGNVELYLHDWGVDFACWCSYKYLNAGAGGIAGAFIHEKHAHTI
KPALVGWFGHELSTRFKMDNKLQLIPGVCGFRISNPPILLVCSLHASLEIFKQATMKALR
KKSVLLTGYLEYLIKHNYGKDKAATKKPVVNIITPSHVEERGCQLTITFSVPNKDVFQEL
EKRGVVCDKRNPNGIRVAPVPLYNSFHDVYKFTNLLTSILDSAETKN SEQ ID NO: 2
Protein 168:
MEPSSLELPADTVQRIAAELKCHPTDERVALHLDEEDKLRHFRECFYIPK
IQDLPPVDLSLVNKDENAIYFNGNSLGLQPKMVKTYLEEELDKWAKIARY
GWRHGKPPWITYDESIVGLMKDIVGANEKEIALMNALTVNLHLLMLSFFK
PTPKRYKILLEAKAFPSDHYAIESQLQLHGLNPEESMRMIKPREGEETLR
IEDILEVIEKEGDSIAVILFSGVHFYTGQHFNIPAITKAGQAKGCYVGWD
LAHAVGNVELYLHDWGVDFACWCSYKLNAGPGGIAGAFIHEKHAHTIKP
ALVGWWGHELSTRFKMDNKLQLIPGVCGFRSSTPPILLVCSLHASLEIFK
QATMKALRKKSVLLTGYLEYLIKHNYGKDKAATKKPVVNIITPSHVEERG
CQLTITFNVPNKDVFQELEKRGVVCDKRNPNGIRVTPVPLYNSFHDVYKF
TNLLTSILDSAETKN*

SEQ ID NO: 3
Protein 153:
MEPSSLELPADTVQRIAAELKCHPTDERVALHLDEEDKLRHFRECFYIPKIQDLPPVDLSL
VNKDENAIYFNGNSLGLQPKMVKTYLEEELDKWAKIARY
GWRHGKPPWITYDESIVGLMKDIVGANEKEIALMNALTVNLHLLMLSFFKPTPKRYKIL
LEAKAFPSDHYAIESQLQLHGLNPEESMRMIKPREGEETLR
IEDILEVIEKEGDSIAVILFSGVHFYTGQHFNIPAITKAGQAKGCYVGFDLAHAVGNVELY
LHDWGVDFACWCSYKLNAGPGGIAGAFIHEKHAHTIKP
ALVGWWGHELSTRFKMDNKLQLIPGVCGFRSSTPPILLVCSLHASLEIFKQATMKALRK
KSVLLTGYLEYLIKHNYGKDKAATKKPVVNIITPSHVEERG
CQLTITFNVPNKDVFQELEKRGVVCDKRNPNGIRVTPVPLYNSFHDVYKFTNLLTSILDS
AETKN*
```

What is claimed is:

1. A method of treating a subject having a tumor, the method comprising administering to the subject a therapeutically effective amount of a modified kynureninase enzyme having an amino acid sequence that is at least 90% identical to the amino acid sequence of SEQ ID NO: 1 and comprising at least one substitution selected from the group consisting of A99R, E103R, V104H, R107P, G112Y, I183P, and I331S.

2. A method of treating a subject having a tumor, the method comprising administering to the subject a therapeutically effective amount of a modified kynureninase enzyme having an amino acid sequence that is the amino acid sequence of SEQ ID NO: 3.

3. The method of claim 1, wherein the amino acid sequence is at least 90% identical to the amino acid sequence SEQ ID NO: 3.

4. The method of claim 1, wherein the modified enzyme comprises:
 (a) the A99R substitution;
 (b) the G112Y substitution;
 (c) the E103R substitution;
 (d) the V104H substitution;
 (e) the I183P substitution; and/or
 (f) the R107P substitution.

5. The method of claim 1, wherein the enzyme further comprises at least one substitution selected from L72N, H102W, F249W, A282P, F306W, S408N, N333T, and A436T.

6. The method of claim 5, wherein the enzyme comprises at least two, at least three, at least four, at least five, or all six of substitutions L72N, H102W, F249W, A282P, F306W, S408N, N333T, and A436T.

7. The method of claim 6, wherein the enzyme comprises the substitutions L72N, H102W, F249W, A282P, F306W, S408N, N333T, and A436T.

8. The method of claim 1, wherein the enzyme has a catalytic activity for kynurenine (KYN) (kcat/kM) of at least 8000 $M^{-1}s^{-1}$.

9. The method of claim 8, wherein the enzyme has a catalytic activity for KYN of between $8000 M^{-1}s^{-1}$ and $40000\ M^{-1}s^{-1}$; $10000 M^{-1}s^{-1}$ and $40000\ M^{-1}s^{-1}$; $20000 M^{-1}s^{-1}$ and $40000\ M^{-1}s^{-1}$; or $25000 M^{-1}s^{-1}$ and $35000\ M^{-1}s^{-1}$.

10. The method of claim 1, wherein the enzyme further comprises a heterologous peptide segment.

11. The method of claim 1, wherein the enzyme is coupled to polyethylene glycol (PEG).

12. The method of claim 11, wherein the enzyme is coupled to PEG at one or more Lys or Cys residues.

13. The method of claim 1, wherein the subject has been identified as having an IDO1, IDO2, or TDO expressing tumor.

14. The method of claim 1, wherein:
 (a) the tumor is a solid tumor or a hematological tumor;
 (b) the subject is a human patient;
 (c) the enzyme is administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage; and/or
 (d) the enzyme is administered with at least a second anti-cancer therapy, optionally wherein the second anti-cancer therapy is radiation therapy, surgical therapy, an immunotherapy, or a second anticancer compound.

15. The method of claim 14, wherein:
 (a) the second anticancer compound is an immune checkpoint inhibitor, optionally wherein the immune checkpoint inhibitor comprises an antibody or antibody-drug conjugate, optionally wherein the antibody is an anti-PD1, anti-CTLA-4, or anti-PD-L1 antibody; and/or (b) the immunotherapy comprises administering immune effector cells or an immunogenic composition to the subject, optionally wherein the immunogenic composition comprises cancer cell antigens and/or wherein the immune effector cells comprise NK-cells, T-cells, or CAR T-cells.

16. The method of claim 2, wherein the subject has been identified as having an IDO1, IDO2, or TDO expressing tumor.

17. The method of claim 2, wherein:
(a) the tumor is a solid tumor or a hematological tumor;
(b) the subject is a human patient;
(c) the enzyme or formulation is administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage; and/or
(d) the enzyme or formulation is administered with at least a second anti-cancer therapy, optionally wherein the second anticancer therapy is radiation therapy, surgical therapy, an immunotherapy, or a second anticancer compound.

18. The method of claim 17, wherein:
(a) the second anticancer compound is an immune checkpoint inhibitor, optionally wherein the immune checkpoint inhibitor comprises an antibody or antibody-drug conjugate, optionally wherein the antibody is an anti-PD1, anti-CTLA-4, or anti-PD-L1 antibody; and/or (b) the immunotherapy comprises administering immune effector cells or an immunogenic composition to the subject, optionally wherein the immunogenic composition comprises cancer cell antigens and/or wherein the immune effector cells comprise NK-cells, T-cells, or CAR T-cells.

* * * * *